United States Patent
Specht et al.

(10) Patent No.: US 11,826,204 B2
(45) Date of Patent: *Nov. 28, 2023

(54) MOTION DETECTION USING PING-BASED AND MULTIPLE APERTURE DOPPLER ULTRASOUND

(71) Applicant: MAUI IMAGING, INC., San Jose, CA (US)

(72) Inventors: Donald F. Specht, Los Altos, CA (US); Kenneth D. Brewer, Santa Clara, CA (US); David M. Smith, Lodi, CA (US); Josef R. Call, Campbell, CA (US); Viet Nam Le, San Jose, CA (US); Bruce R. Ritzi, Sunnyvale, CA (US)

(73) Assignee: MAUI IMAGING, INC., San Jose, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 16/298,767

(22) Filed: Mar. 11, 2019

(65) Prior Publication Data
US 2019/0200961 A1 Jul. 4, 2019

Related U.S. Application Data

(63) Continuation of application No. 13/690,989, filed on Nov. 30, 2012, now Pat. No. 10,226,234.
(Continued)

(51) Int. Cl.
*A61B 8/08* (2006.01)
*A61B 8/00* (2006.01)
(Continued)

(52) U.S. Cl.
CPC ............ *A61B 8/488* (2013.01); *A61B 8/4444* (2013.01); *A61B 8/4488* (2013.01); *A61B 8/461* (2013.01);
(Continued)

(58) Field of Classification Search
CPC .. G01S 15/586; G01S 15/582; G01S 15/8984; G01S 15/8979; G01S 15/89;
(Continued)

(56) References Cited

U.S. PATENT DOCUMENTS 5,060,205 A 10/1991 Phelan
5,666,953 A 9/1997 Wilk
(Continued)

FOREIGN PATENT DOCUMENTS

EP 1346689 A2 9/2003
JP 2005046193 A 2/2005
(Continued)

OTHER PUBLICATIONS

Holzner, Steven. "How to Find Vector Components", https://www.dummies.com/education/science/physics/how-to-find-vector-components/, retrieved Mar. 4, 2021.*
(Continued)

*Primary Examiner* — Carolyn A Pehlke
(74) *Attorney, Agent, or Firm* — Shay Glenn LLP

(57) ABSTRACT

A method of full-field or "ping-based" Doppler ultrasound imaging allows for detection of Doppler signals indicating moving reflectors at any point in an imaging field without the need to predefine range gates. In various embodiments, such whole-field Doppler imaging methods may include transmitting a Doppler ping from a transmit aperture, receiving echoes of the Doppler ping with one or more separate receive apertures, detecting Doppler signals and determining the speed of moving reflectors. In some embodiments, the system also provides the ability to determine the direction of motion by solving a set of simultaneous equations based on echo data received by multiple receive apertures.

9 Claims, 19 Drawing Sheets

Related U.S. Application Data

(60) Provisional application No. 61/691,717, filed on Aug. 21, 2012, provisional application No. 61/565,796, filed on Dec. 1, 2011.

(51) Int. Cl.
  *G01S 15/89* (2006.01)
  *G01S 7/52* (2006.01)
  *A61B 8/14* (2006.01)

(52) U.S. Cl.
  CPC .......... *A61B 8/5207* (2013.01); *A61B 8/5223* (2013.01); *G01S 15/8913* (2013.01); *G01S 15/8927* (2013.01); *G01S 15/8984* (2013.01); *A61B 8/145* (2013.01); *A61B 8/4477* (2013.01); *A61B 8/463* (2013.01); *G01S 7/52066* (2013.01); *G01S 7/52071* (2013.01)

(58) Field of Classification Search
  CPC ............. G01S 15/8988; G01S 15/8927; G01S 15/8913; A61B 8/00; A61B 8/488; A61B 8/4444; A61B 8/4494; A61B 8/4488; A61B 8/461; A61B 8/5207; A61B 8/5223; A61B 8/145; A61B 8/4483; A61B 8/467; A61B 8/523; A61B 8/5246; A61B 8/06; A61B 8/481; A61B 8/44
  See application file for complete search history.

(56) References Cited

U.S. PATENT DOCUMENTS

| | | | |
|---|---|---|---|
| 5,817,023 A | 10/1998 | Daft | |
| 6,190,318 B1 | 2/2001 | Bab et al. | |
| 6,464,637 B1* | 10/2002 | Criton | A61B 8/06 |
| | | | 600/441 |
| 6,490,477 B1 | 12/2002 | Zylka et al. | |
| 6,629,929 B1 | 10/2003 | Jago et al. | |
| 6,645,147 B1 | 11/2003 | Jackosn et al. | |
| 2003/0163271 A1 | 9/2003 | Chell et al. | |
| 2003/0181806 A1 | 9/2003 | Medan et al. | |
| 2004/0258127 A1 | 12/2004 | Ramamurthy et al. | |
| 2007/0043290 A1 | 2/2007 | Goepp et al. | |
| 2007/0161904 A1* | 7/2007 | Urbano | A61B 8/565 |
| | | | 600/459 |
| 2008/0110263 A1* | 5/2008 | Klessel | A61B 8/4483 |
| | | | 310/322 |
| 2008/0319318 A1 | 12/2008 | Johnson et al. | |
| 2009/0005679 A1 | 1/2009 | Dala-Krishna | |
| 2009/0326379 A1* | 12/2009 | Daigle | A61B 8/06 |
| | | | 600/453 |
| 2011/0196237 A1* | 8/2011 | Pelissier | A61B 8/467 |
| | | | 600/454 |
| 2012/0209150 A1 | 8/2012 | Zeng et al. | |
| 2013/0030296 A1 | 1/2013 | Miyaki | |
| 2013/0237799 A1 | 9/2013 | Motoki | |

FOREIGN PATENT DOCUMENTS

| | | |
|---|---|---|
| KR | 1020140069664 A | 6/2014 |
| WO | WO2008/137030 A1 | 11/2008 |
| WO | WO2011/094585 A | 8/2011 |

OTHER PUBLICATIONS

Scabia, M., M. Calzolai, L. Capineri, Leonardo Masotti, and A. Fort. "A real-time two-dimensional pulsed-wave Doppler system." Ultrasound in medicine & biology 26, No. 1 (2000): 121-131.*

Dunmire, B., et al. "Cross-beam vector Doppler ultrasound for angle-independent velocity measurements." Ultrasound in medicine & biology 26.8 (2000): 1213-1235.*

Pinghua; Optimization of Key Parameters of Phased array Ultrasonic Testing; Dalian University of Technology; Masters Dissertation; No. 7; retrieved from the internet (http://www.cnki.net); 69 pages; Jul. 15, 2012.

* cited by examiner

MOTION DETECTION USING PING-BASED AND MULTIPLE APERTURE DOPPLER ULTRASOUND

CROSS REFERENCE TO RELATED APPLICATIONS

This application is a continuation of U.S. patent application Ser. No. 13/690,989, filed Nov. 30, 2012, now U.S. Pat. No. 10,226,234, which application claims the benefit of U.S. Provisional Patent Applications No. 61/565,796, filed Dec. 1, 2011, titled "Doppler Ultrasound Imaging Using a Multiple Aperture Probe," and 61/691,717, filed Aug. 21, 2012, titled "Ultrasound Imaging System Memory Architecture," both of which are incorporated herein by reference.

This application is related to U.S. patent application Ser. No. 11/865,501, filed Oct. 1, 2007, titled "Method And Apparatus To Produce Ultrasonic Images Using Multiple Apertures," now U.S. Pat. No. 8,007,439; U.S. patent application Ser. No. 13/002,778, filed Apr. 6, 2011, titled "Imaging With Multiple Aperture Medical Ultrasound And Synchronization Of Add-On Systems," now U.S. Pat. No. 8,602,993; U.S. patent application Ser. No. 12/760,375, filed Apr. 14, 2010, titled "Universal Multiple Aperture Medical Ultrasound Probe," now abandoned, U.S. patent application Ser. No. 12/760,327, filed Apr. 14, 2010, titled "Multiple Aperture Ultrasound Array Alignment Fixture," now U.S. Pat. No. 8,473,239; U.S. patent application Ser. No. 13/272,098, filed Oct. 12, 2011, titled "Multiple Aperture Probe Internal Apparatus and Cable Assemblies," now U.S. Pat. No. 9,788,813; U.S. patent application Ser. No. 13/272,105, filed Oct. 12, 2011, titled "Concave Ultrasound Transducers and 3D Arrays," now U.S. Pat. No. 9,247,926; and U.S. patent application Ser. No. 13/029,907, filed Feb. 17, 2011, titled "Point Source Transmission And Speed-Of-Sound Correction Using Multi-Aperture Ultrasound Imaging," now U.S. Pat. No. 9,146,313.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure generally relates to medical imaging, and more particularly to Doppler ultrasound imaging using a probe with multiple apertures.

BACKGROUND

Doppler methods in medical ultrasound encompass a number of related techniques for imaging and quantifying blood flow. For stationary targets, the round trip travel time of an ultrasound pulse transmitted from a transducer, reflected from the target, and returned back to the transducer is the same for each transmitted pulse. In the case of a moving object, successive echographic returns will arrive at different times with respect to the transmit pulse. For example, echographic returns that are received at intervals less than the stationary round-trip time may represent reflectors moving towards the TX/RX probe, while returns received at intervals longer than the stationary round-trip time may represent reflectors moving away from the TX/RX probe. This is the result of the well-known Doppler Effect, which may also be described in terms of relative frequencies. In the frequency domain reflected signals received at a higher-than-expected frequency may represent reflectors moving towards the transmitter/receiver, while reflected signals received at a lower-than-expected frequency may represent reflectors moving away from the transmitter/receiver. From this information, the velocity of the moving reflector can be estimated.

Conventional ultrasound (or "scanline based" ultrasound as used herein) utilizes a phased array controller to produce and steer a substantially linear transmit waveform. In order to produce a B-mode image, a sequence of such linear waveforms (or "scanlines") may be produced and steered so as to scan across a region of interest. Echoes are received along each respective scanline. The individual scanlines may then be combined to form a complete image.

Because a traditional scanline-based ultrasound path is directional (along the scanline axis), only motion along a scanline axis produces a Doppler (motion) signal. Flow that is transverse to the scanline is not detectable using such conventional methods, and thus the velocity magnitudes obtained in conventional Doppler methods represent only the component of the flow velocity vector that lies along the transmit/receive scanline axis. In order to estimate the true magnitude of the flow velocity vector, Vector Doppler methods are employed. These methods rely on data from multiple intersecting scanlines to estimate the direction of the flow vector and the flow velocity vector.

Several scanline-based Doppler methods have been developed to present different aspects of blood flow. Typically, "spatial imaging" (otherwise referred to as "B-mode" imaging or "sector scan" imaging) of the flow field is used to locate vessels, to measure their size, and to observe flow structure. "Flow imaging" is used in conjunction with echographic imaging in a "duplex" mode that combines both types of images in an overlay, with echographic amplitude presented in grayscale and flow velocity rendered in color.

A sonographer may obtain a detailed quantification of flow velocity by selecting a much smaller sample volume chosen within the region of interest. The smallest volume that can be sampled and processed independently is given by the axial length (the transmit pulse length) and the lateral beam widths (in and out of the imaging plane) of the scanline beam. Using scanline-based Doppler methods, this small sample volume, also known as a "range gate," a "Doppler gate" or a "Doppler range gate" must be defined by a sonographer via a user interface prior to transmission and receipt of Doppler ultrasound signals. This requirement for predefining a Doppler range gate means that moving reflectors that lie outside of the predefined range gate may not be identified without defining a new range gate, which may require conducting a separate Doppler imaging session.

Scanline-based Doppler imaging can also impose substantial limits on the frame-rate of B-mode images within a scanline-based ultrasound imaging system. The frame rate of a scanline-based ultrasound imaging system is the pulse-repetition frequency (PRF, which is limited by the round-trip travel time of ultrasound in the imaged medium) divided by the number of scanlines per frame. Typical scanline-based ultrasound imaging systems use between about 64 and about 192 scanlines per frame. Typically, an ensemble of between 8 and 32 pulse-echo events is used for each Doppler scanline in the region of interest. Such Doppler ensembles are effectively an interruption to a B-mode sector scan, resulting in a lower B-mode frame rate (or requiring fewer scanlines per B-mode frame) than the system would otherwise be capable of.

SUMMARY OF THE DISCLOSURE

In one aspect there is provided a method of conducting Doppler ultrasound by selecting a transmit aperture from a plurality of transducer elements of a transducer array. Next, transmitting an unfocused ultrasound signal from the transmit aperture into a region of interest and then receiving echoes of only the unfocused ultrasound signal on a first receive aperture. There is also a step of storing the received echoes in a memory device. Then there is a step of beamforming the received echoes to determine a display position for each of a plurality of reflectors within the region of interest. A step of selecting a first test segment from the received echo data of the region of interest and also detecting a Doppler frequency shift within the echoes of the receiving step of at least one of the plurality of reflectors. There is also a step of determining a speed of the at least one reflector within the first test segment. Finally, there is a step of displaying motion information of the at least one reflector in an image wherein the motion information is based in part on the detecting step and the determining step.

The method may also optionally include in the determining step the step of determining a direction of motion of the at least one reflector within the first test segment. In one aspect of the method there is a step of selecting a second test segment and thereafter repeating the steps of selecting, detecting, determining and displaying for at least one of the plurality of reflectors within the second test segment.

In still another aspect, the method may also include selecting a second test segment wherein the second test segment is a portion of the region of interest outside of the portion of the region of interest within the first test segment. In some embodiments, the selecting transmitting and receiving steps are performed without a predefined range gate for the unfocused ultrasound signal. In one aspect, the beamforming step is performed before the detecting step. In another aspect, the detecting step is performed before the beamforming step. In still other aspects, the selecting a test segment step is selected based on a pixel position within the region of interest. Still further, some aspects may proceed whereby the selecting a test segment step is performed manually by a user based on a correlation with a b-mode image and information from the receiving step.

In some additional alternatives, selecting a test segment step is performed automatically by an imaging system. In still another aspect, there may be included a step of systematically evaluating each test segment within a region of interest. This step of evaluating every test segment within the received echoes of only the unfocused ultrasound signal. In still further aspects, there is a step of selecting a test segment based on a computer aided detection analysis of a contemporaneous B-mode image of the region of interest and correlated position information within the region of interest. In some aspects, the step of selecting a test segment is performed based on a timing between the signals in the receiving step. In still other aspects, the step of selecting a test segment is based in part on a time range corresponding to a depth range of interest within the target area. Still further, a step of selecting a test segment is performed by evaluating all test segments within the region of interest.

In still other additional embodiments, there is also a step of receiving echoes on a second receive aperture separate from the first receive aperture. In another alternative, there is a process of computing an adjustment factor for each pixel imaged by the acoustic path to the first receive aperture and for each pixel imaged by the acoustic path to the second receive aperture. There may also be provided a method of obtaining an improved speed measurement by applying the adjustment factor to the result of the determining step. In some aspects, there is an adjustment factor is $1/\cos(\Phi/2)$ where $\Phi$ is an angle between a transmitter-to-reflector line and a receiver-to-reflector line for angles defined using a position of the transmit aperture, a position of each pixel imaged and positions of each of the first receive aperture and the second receive aperture. In others there is a method of combining an adjusted speed measurement obtained from the first receive aperture with an adjusted speed measurement obtained from the second receive aperture for a moving reflector. In still others, there is a method of solving simultaneous equations including using a position of the first receive aperture and a speed measurement obtained using the first receive aperture and a position of the second receive aperture and a speed measurement obtained using the second receive aperture to obtain a velocity vector representing a direction and a magnitude of motion of a first reflector. In other aspects, there is also a method of solving a second set of simultaneous equations including using a position of the first receive aperture and a speed measurement obtained using the first receive aperture and a position of a third receive aperture and a speed measurement obtained using the third receive aperture to obtain a second velocity vector representing a direction and a magnitude of motion of the first reflector. In another aspect, there is also a step of averaging the first velocity vector and the second velocity vector to obtain a new velocity vector describing speed and direction of motion of the first reflector.

In some additional aspects, there is also a method of calculating a first plurality of velocity vectors for a plurality of reflectors using velocity measurements from a first acoustic path and a second different acoustic path. In some aspects, there is a step of performing an averaging operation of each of the velocity vectors for the plurality of reflectors to determine a predominant direction of movement for the plurality of reflectors. In some aspects, there is a step applying a color to each non-zero velocity reflector of the plurality of reflectors related to a component of the velocity vector along a predominant motion axis. Still further alternatives may provide methods for calculating a second plurality of velocity vectors obtained from the first acoustic path and a third acoustic path; and averaging the first plurality of velocity vectors and the second plurality of velocity vectors. In still other embodiments, there may also be additional steps for applying an adjustment factor prior to the step of solving simultaneous equations. In some aspects, the step of transmitting may include transmitting an unfocused ultrasound signal having a pulse width of more than about seven cycles at a selected frequency or in another aspect, transmitting an unfocused ultrasound signal having a frequency that is lower than a frequency used for B-mode imaging.

In additional alternative aspects of a method of imaging with Doppler ultrasound there is provided a step of transmitting a first unfocused semicircular ultrasound wavefront pulse from a first transmit aperture towards a moving object. Next there is a step receiving echoes of the first wavefront pulse at a first receive aperture and receiving echoes of the first wavefront pulse at a second receive aperture. Thereafter, there is a step of computing an object velocity vector at one or more test segments based on the received echoes at the first and second receive apertures. In one aspect, there is also a process of computing a minimum object velocity using data independent approximations for each pixel in an image. Still other aspects provide for data independent approximation comprises multiplying a first measured velocity value by an inverse of a cosine of half of a first angle defined by the transmit aperture, a first test segment and the second receive aperture. Still other alternatives provide for computing speed and direction of the moving reflector by solving a set of simultaneous equations based on geometry of a multiple aperture probe. There may also be aspects for computing a direction of the velocity vector, or computing a magnitude of the velocity vector, in some exemplary embodiments. In one aspect, there is a magnitude of the velocity vector is calculated by taking half the sum of the magnitudes of a first velocity measurement and a second velocity measurement; the first velocity measurement taken along an acoustic path bisecting an angle between the first receive aperture, a test segment, and the second receive aperture; and the second velocity measurement taken along an acoustic path from a transmit aperture to a test segment, to the second receive aperture.

In still other aspects, there is a step of receiving a user input indicating an axis of predominant motion of the moving object.

In still other aspects there is provided a step of displaying at least one color to indicate motion along the indicated axis of predominant motion. Additionally, there may also be aspects of these methods for automatically analyzing a plurality of measured velocity vectors to identify at least one axis of predominant motion.

In another alternative embodiment, there is provided a method of measuring a velocity of objects moving within a region of interest by transmitting a first unfocused semicircular ultrasound wavefront pulse from a first transmit aperture. There is also steps of receiving echoes of the first wavefront pulse at a first receive aperture; storing in-phase values of the received echoes; storing quadrature values of the received echoes; and evaluating the in-phase and quadrature values to determine a magnitude and a direction of motion of objects within the region of interest relative to the first transmit aperture or the first receive aperture. In one aspect, the transmit aperture and the receive aperture are located on a common transducer array. In another aspect, there is a step of also receiving echoes of the first wavefront pulse at a second receive aperture that is separate from the first receive aperture, and storing in-phase and quadrature values of the received echoes.

In another alternative embodiment, there is provided a method of detecting and displaying motion of an object imaged with a multiple aperture ultrasound imaging system including a step of transmitting a sequence of unfocused semicircular ultrasound pulses from a transmit aperture of a multiple aperture ultrasound probe. There is also a step of separately receiving echoes from each pulse of the sequence with a receive aperture of the multiple aperture ultrasound probe. In one aspect, there is an imaging frame rate that is equal to a rate at which consecutive unfocused semicircular ultrasound pulses are transmitted in the transmitting step. Aspects also include the step of forming a sequence of complete image frames from the echoes of each transmit pulse, analyzing differences in consecutive image frames to detect motion of imaged objects and additionally or alternatively a step of displaying an image of the object and highlighting the detected motion. In some aspects, the highlighting comprises applying a color to motion along an axis of predominant motion.

In still another aspect, there is a method of producing an ultrasound image indicating motion by retrieving a first data set from a non-volatile digital memory device, the first data comprising position and orientation information of a transmit aperture and retrieving a second data set from a non-volatile digital memory device, the second data set comprising a series of echo magnitude values resulting from echoes of a sequence of transmitted Doppler ping signals. Thereafter, there is a step of detecting Doppler shift frequencies within at least a portion of the second data set based on a first set of Doppler detection parameters. In some aspects, there is a step of determining a position of at least one moving reflector based on a second set of beamforming parameters, wherein at least one parameter has a value different than a value used during a live imaging session in which the echo data was captured. In additional aspects, the first set of parameters or the second set of parameters includes one or more of: a transmit aperture definition, a receive aperture definition, a test segment, a predominant direction axis, a relative movement threshold value to characterize a fast movement value over a slow movement value, a Doppler motion estimation algorithm, a speed-of-sound assumption, one or more weighting factors, a de-convolution filtering value, a matched filtering value, a calibration data value, or a transmission data value. In still further alternative aspects, the Doppler detection parameters include at least one of a test segment definition, a predominant direction axis definition, a minimum speed threshold value, and a Doppler motion estimation algorithm. In still other additional aspects, the beamforming parameters include at least one of a speed-of-sound value, a weighting factor, an applied filter type, a probe calibration datum, and a datum describing an ultrasound transmit signal.

In still another additional or alternative aspect, there is provided a method of conducting Doppler ultrasound by transmitting a first single unfocused ultrasound signal into a target object. Next, there is a step of receiving echoes of the first single unfocused ultrasound signal. Then there is a step of detecting motion in at least two separate regions of the target object from the echoes of the first single unfocused ultrasound signal. In some aspects, there may also be a step of performing the receiving step with one or more receive without using an aperture used to perform the transmitting step. Still other aspects may also perform beamforming of the received echoes to determine a display position for each of a plurality of reflectors within a region of interest containing the target object. In still other aspects, there may also be for the detecting motion step a further detecting a Doppler frequency shift of at least one pixel within the received echoes of the first single unfocused ultrasound signal. In another aspect, the selecting and transmitting and receiving steps are performed without a predefined range gate for the first single unfocused ultrasound signal. In still another aspect, the beamforming step is performed before the detecting step. In still another aspect, the beamforming step is performed after the detecting step.

In still another aspect, there is provided a method of detecting Doppler shift according to any of the above embodiments whereby the shift of any test segment designated on a related b-mode image by beamforming images from the echo returns from each ping or unfocused ultrasound signal. Thereafter, estimating the Doppler frequency shift based on a sequence of samples for each ping at the test segment.

A method of detecting Doppler shift according at any of the above embodiments whereby a test segment designated as a time of response after ping initiation at a receive element. Thereafter, using only the time of detection of Doppler data at each receiver as input to a beamformer for Doppler and then color coding the beamformed Doppler according to direction and/or frequency. Thereafter, in one aspect, there is a step of superimposing the color information on the B-mode image. In one alternative aspect, instead of using the times of Doppler detection directly as input to a beamformer for Doppler, the method proceeds using the Doppler detection times to select the raw echo segments to use as input to the beamformer for Doppler. In a still further aspect, there is a step of selecting echo segments to provide coherent addition for improved lateral resolution of a resulting image.

It is to be appreciated that the methods of any of the above embodiments described above or herein may be provided as or performed using computer readable instructions or code containing the steps for execution using one or more computer based ultrasound signal processing systems using software, firmware or hardware configured for such operations and processing.

It is to be appreciated that above illustrative aspects, embodiments, alternatives and steps may also be combined to provide still further alternative embodiments of the inventive methods described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
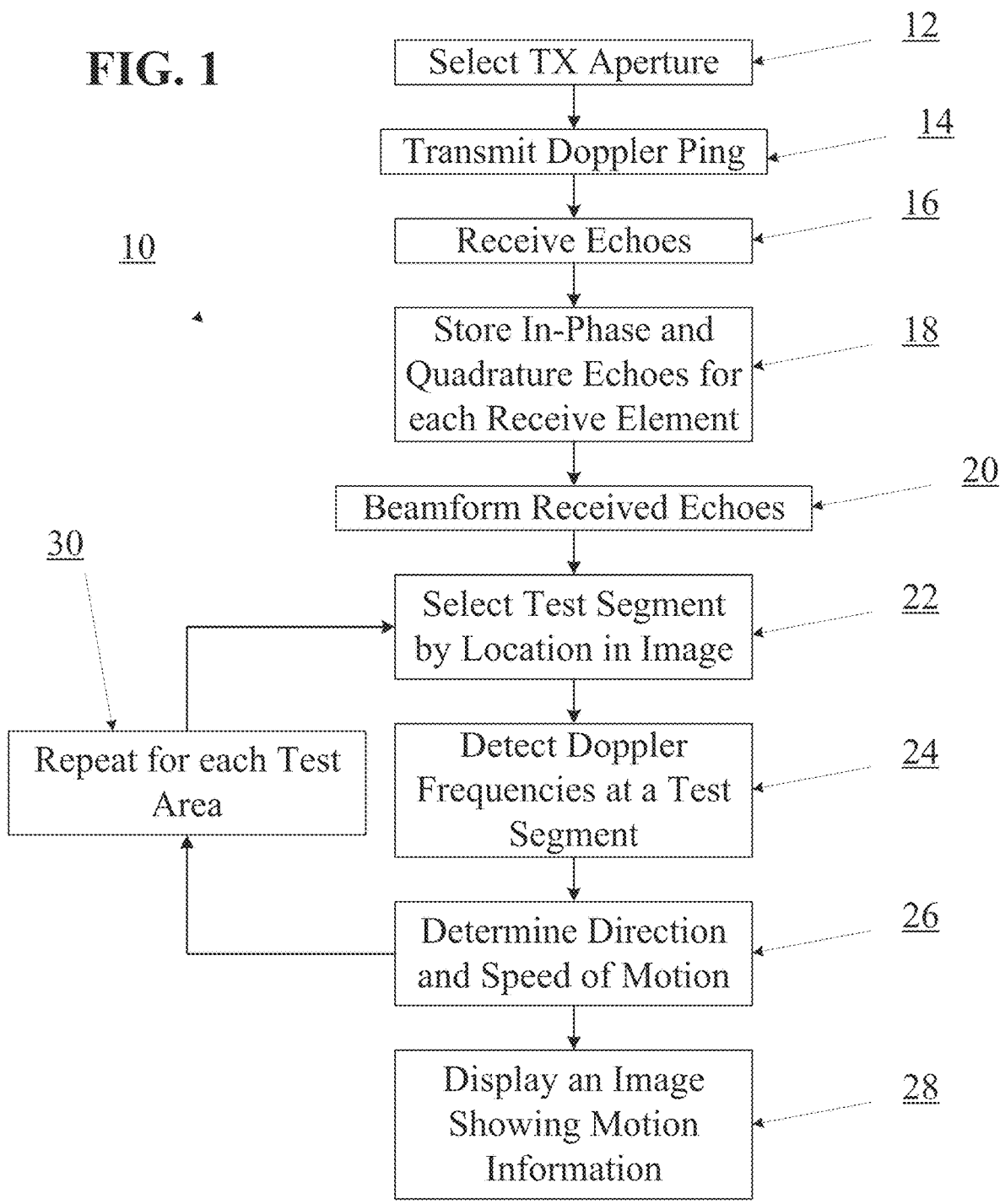
FIG. 1 is a flow chart illustrating an embodiment of a process for detecting motion using a ping-based Doppler ultrasound imaging technique.

The methods and apparatus described herein solve many problems of Doppler in ultrasound today. Using conventional scanline-based Doppler, a sonographer is faced with trying to satisfy the conflicting requirements of positioning an ultrasound probe to obtain the best B-mode image and also positioning the probe to have a scanline beam aligned with blood flow in a vessel. A second problem with conventional Doppler is that the field of view of the Doppler must be restricted by predefining a Doppler range gate so that the pulse repetition frequency on the selected scan line(s) can be high enough to be sensitive to the Doppler frequencies.

Some embodiments of the methods and systems described herein use ping-based Doppler imaging techniques in which unfocused semi-circular (or cylindrical) ultrasound pulses with relatively long pulse lengths (Doppler pings) are used to insonify an entire field of view in each Doppler ping so that Doppler frequencies can be detected anywhere in the B mode field of view without the need to predefine Doppler range gates. Furthermore, both the speed and direction of moving reflectors can be detected without the need to align the probe relative to the direction of motion. In some embodiments, the use of a multiple aperture ultrasound probe may further allow for the detection of two-dimensional motion vectors. Various embodiments of multiple aperture ping-based Doppler and B-mode imaging may simultaneously improve the lateral resolution of B mode images and the accuracy of Doppler velocity estimation.

Using conventional scanline-based Doppler imaging, pulsed Doppler signals are typically produced by transmitting a focused scanline beam and receiving echoes with a receiver focused along the same scanline. Using such systems, range gates must be defined along the scanline prior to transmitting and receiving ultrasound signals in order to define the depth of a region of interest in which motion information is to be detected. Samples of the echoes from within the range gate are taken while successive pulses are transmitted along the same scan line. These samples are then evaluated to detect Doppler frequencies indicating motion.

Ultrasound imaging systems using multiple aperture probes are shown and described in U.S. Pat. No. 8,007,439 and U.S. Patent Application Publication Nos. Applications 2010-0262013-A1; 2010-0268503-A1; and 2011-0201933-A1. The embodiments below provide systems and methods for performing Doppler velocity measurement and imaging utilizing multiple aperture probes and systems such as those shown and described in Applicant's previous patent applications and in the drawings and specification herein.

Although various embodiments are described herein with reference to ultrasound imaging of various anatomic structures, it will be understood that many of the methods and devices shown and described herein may also be used in other applications, such as imaging and evaluating non-anatomic structures and objects. For example, the ultrasound probes, systems and methods described herein may be used in non-destructive testing or evaluation of various mechanical objects, structural objects or materials, such as welds, pipes, beams, plates, pressure vessels, layered structures, etc. Furthermore the various embodiments of systems and methods for assessing movement or velocity of an imaged object or substance may also be applied to non-medical scenarios such as measuring the velocity of fluid moving through a pipe, pressure vessel or other fluid-carrying conduit or container. Therefore, references herein to medical or anatomic imaging targets such as blood, blood vessels, heart or other organs are provided merely as non-limiting examples of the nearly infinite variety of targets that may be imaged or evaluated using the various apparatus and techniques described herein.

Introduction to Ping-Based Doppler Ultrasound Techniques

The various embodiments described herein with reference to the accompanying figures provide systems and methods for detecting, estimating and characterizing the velocity of moving objects using ping-based Doppler imaging and ping-based B-mode imaging techniques. Some embodiments provide further advantages with the combination of ping-based imaging techniques with multiple aperture ultrasound probes and imaging techniques as will be described in further detail below.

When using a ping-based ultrasound imaging technique, both timing information and frequency information may be collected from reflector echoes returning to receive transducer elements following a transmitted ping. The position of echoes may be determined from the timing information by a ping-based beamforming process (as described elsewhere herein and in Applicants' prior applications referenced above), while the velocity of moving reflectors may be determined from the frequency information by applying Doppler principles. Thus, both the position and the velocity of every reflector within an insonified region may be determined from a single transmit ping. Accuracy and resolution may be improved by combining information obtained from multiple pings.

Figure 2:
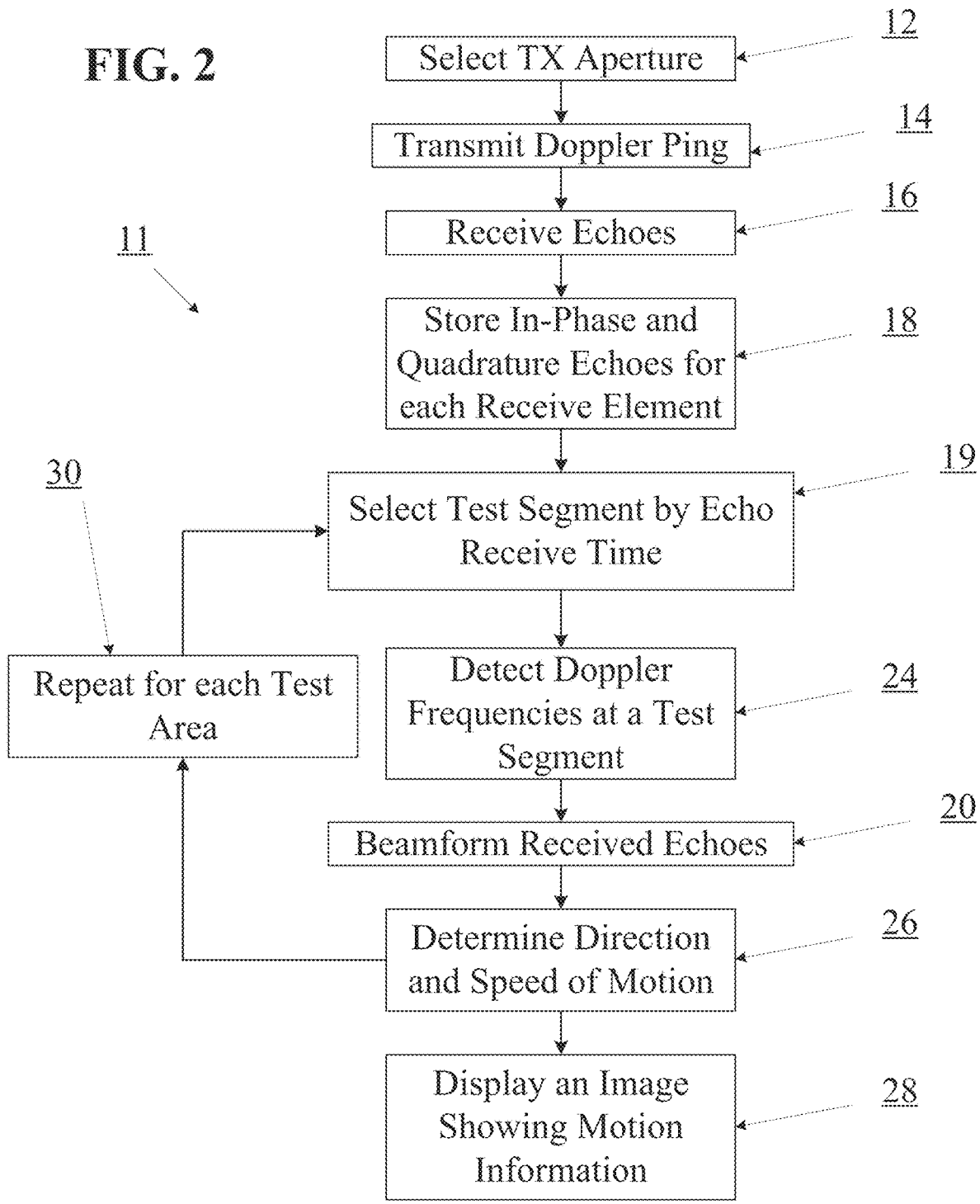
FIG. 2 is a flow chart illustrating another embodiment of a process for detecting motion using a ping-based Doppler ultrasound imaging technique.

With reference to FIGS. 1 and 2, an overview of some embodiments of ping-based and ping-based multiple aperture motion detection processes will now be provided. Further details and embodiments of the various process steps will be provided in subsequent sections below with reference to additional figures.

FIG. 1 illustrates an embodiment of a ping-based Doppler motion detection/imaging process 10 in which an imaging system may automatically cycle through a plurality of spatially-defined "test segments" in order to identify sections of an insonified region of interest that contain moving reflectors. In some embodiments, echo data corresponding to each pixel of a final image may be treated as a separate test segment. The process of FIG. 1 may begin with the selection of a transmit (TX) aperture 12. An ideal transmit aperture will be one that provides an unobstructed view of a region of interest (i.e., unobstructed by ribs or other obstacles). In various embodiments, a suitable TX aperture (as described below) may be selected by an automatic process or a manual process.

Once a TX aperture is selected 12, a first Doppler ping may be transmitted 14 into the region of interest. Echoes of the first Doppler ping may be received 16 using one or more receive apertures (depending on the construction of the probe being used and whether or not 2-dimensional Doppler detection is to be used as will be described below). Received echoes may be stored 18 separately for each receive transducer element. In some embodiments, echoes received by each receive aperture may be stored in two or more separate data streams 18. The first data stream may represent in-phase echoes and a second data stream may represent "quadrature" echoes which represent the same received waveform sampled at a time delay equivalent to about 90 degrees ($\pi/2$ radians) relative to the in-phase data. In other embodiments, similar results may be achieved by other methods such as oversampling received echo data streams. Alternatively, delays other than ~90 degrees may also be used. In some embodiments, if processing hardware is sufficient to process echo data without substantial delay, the step of storing echo data may be omitted.

In the embodiment of FIG. 1, the received Doppler echoes may then be beamformed 20 to determine the position of each reflector (moving or not) within the region of interest. In some embodiments, a ping-based beamforming technique such as that described below may be used. Once Doppler echoes have been beamformed 20, a test segment (i.e., a finite segment of the received echo data in which Doppler shift signals will be sought) may be selected. In the process 10 of FIG. 1, such test segments may be defined 22 with reference to the position of the corresponding reflectors within a region of interest. In some embodiments, an imaging system may automatically select a test segment 22. For example, in some embodiments, an imaging system may be configured to cycle through all possible test segments in an insonified region of interest. In other embodiments, an imaging system may be configured to allow for selection 22 of one or more test segments based on positions correlated with positions in a contemporaneous B-mode image of the same region of interest. In some such embodiments, any number of regions of any size may be selected 22 by a user from a displayed B-mode image, and corresponding regions in the Doppler data may be treated as one or more test segments. In other embodiments, automatic heuristics may be used to recognize known features (such as blood vessels, organs or other structures) and to automatically select 22 test segments based on portions of those recognized features in which motion may be expected or sought.

Once a first test segment is selected 22 (whether manually or automatically), the echoes of reflectors within the test segment may be evaluated to detect any Doppler frequencies 24 that may be present. In some embodiments, Doppler frequencies may be detected 24 using any of the methods described below with reference to FIGS. 9A and 9B. In alternative embodiments, other methods of detecting Doppler frequencies may also be used.

Once Doppler frequencies are identified 24 within a test segment, the data may be further analyzed to determine 26 the speed and direction of the moving reflector. In some embodiments, the step of determining the speed 26 of the moving reflector may involve applying a threshold test to determine whether the reflector is moving faster than a threshold speed. In other embodiments, a size, intensity or frequency threshold test may be applied to determine whether the moving reflector is larger than a threshold size, at least as intense as a threshold intensity, or falls within a specified frequency range. For example, blood vessels tend to appear darker than surrounding tissues in a B-mode image. As a result, relatively longitudinal "dark" areas surrounded by "lighter" areas may be selected as good candidate test segments in which to seek motion information. In some embodiments, reflectors failing a threshold test may be ignored in subsequent steps. In some embodiments, the speed of a moving reflector may be detected using the methods described below. In alternative embodiments, other methods of quantifying the speed of a moving reflector based on the Doppler shift principle may also be used.

In some embodiments, the direction of a moving reflector may be detected 26 one-dimensionally relative to the ultrasound probe. In such one-dimensional motion detection embodiments, motion may be characterized as moving "towards" or "away from" the probe. Some embodiments of such one-dimensional motion detection methods are described below. Any other suitable method may also be used.

In other embodiments, when echoes are received by receive transducer elements on at least two separate apertures, the direction of a moving reflector may be characterized 26 as a two-dimensional vector within the image plane. Details of some embodiments of such a two-dimensional motion detection method are described below with reference to FIG. 16. Other two-dimensional motion detection methods may also be used.

The steps of selecting a test segment 22, detecting Doppler frequencies 24, and determining the speed and direction of moving reflectors 26 may be repeated 30 as many times as needed or desired until all test segments to be tested have been evaluated. If sufficient data processing hardware is available, multiple test segments may be evaluated in parallel rather than sequentially.

Once the direction and speed of moving reflectors in all selected test segments has been determined 26, such information may be compiled into an image that may be overlaid or otherwise combined with a B-mode image for display to a user. In other embodiments, motion information may be presented numerically, as a graph or otherwise without necessarily producing an image to be combined with a B-mode image.

FIG. 2 illustrates an alternative embodiment of a ping-based Doppler motion detection/imaging process 11. The process 11 of FIG. 2 is substantially similar to that of FIG. 1, but the sequence of the steps of beamforming received echoes 20 and detecting Doppler frequencies 24 are reversed in the process 11 of FIG. 2 relative to the sequence of those steps in the process 10 of FIG. 1.

In the process 11 of FIG. 2, Doppler frequencies may be detected 24 in echoes prior to beamforming to determine the position of reflectors causing the echoes. The sequence of FIG. 2 means that the positions of reflectors are not necessarily known prior to selection 19 of a "test segment" to be evaluated for the presence of Doppler frequencies. This merely means that the step of selecting 19 a test segment may be performed with reference to a range of echo receive times for a given echo data stream. Alternatively, as in previously-described embodiments, rough correlations between the receive times of received echoes and positions of the corresponding reflectors in a B-mode image may be made. For example, because the time at which an echo is received is generally correlated with the depth of a reflector, a range of test segments may be defined in terms of depth relative to the probe, and such depth information may be translated into a range of echo receive times. In some such cases, selection of a test segment may proceed in substantially the same ways as described above, at least from the perspective of a user. In fully automated embodiments, an imaging system may be configured to identify test segments 19 as discrete segments of an echo data stream for a particular receive element.

Once moving reflectors are identified based on the Doppler detection step 24, the echoes corresponding to the moving reflectors may be beamformed to determine their position within the region of interest. In some embodiments, the beamforming of Doppler echo data may be limited to determining the position of only those reflectors that have been identified as moving faster than a threshold speed (or those passing some other threshold test). In other embodiments, selection of reflectors from the Doppler echo data to be beamformed may be subject to any other filters or limitations as desired.

Once the Doppler echoes have been beamformed, the echo data may be evaluated to determine a speed and direction of the corresponding moving reflectors. Such speed and direction detection may be performed one-dimensionally or two-dimensionally as described in further detail below.

Alternatively, in some embodiments, if the step of detecting the direction of motion 26 is to be performed in only one dimension in a process 11 such as that shown in FIG. 2, the beamforming step 20 may be performed after the direction detection step 26. This is due to the fact that one-dimensional direction detection does not require information about the position of reflectors within the region of interest.

In some embodiments, all of the steps (e.g., 19-30) following the step of storing echo data 18 may be performed using only echo data retrieved from memory. In such embodiments, various adjustments may be made to the sequence of steps, the assumptions made or other factors affecting the processing of Doppler echo data. Such adjustments may be made iteratively until a desired level of quality is reached. An example of a process for re-processing raw Doppler echo data retrieved from memory is described below with reference to FIG. 21. In some embodiments, such processing may be performed using data processing hardware that is entirely independent of an ultrasound imaging system used to transmit and receive ultrasound signals. Such alternative processing hardware may comprise a desktop computer, a tablet computer, a laptop computer, a smartphone, a server or any other general purpose data processing hardware.

Embodiments of Multiple Aperture Ultrasound Imaging Processes

Multiple aperture ultrasound imaging generally involves the use of ultrasound probes having a total width that is much greater than is possible with conventional ultrasound techniques. Multiple aperture ultrasound imaging involves transmitting ultrasound signals from a small number of transducer elements, and receiving echoes using a much larger number of transducer elements. By arranging the receive transducer elements into a plurality of receive apertures and performing various processing and combining steps, ultrasound images may be formed with a lateral resolution that dramatically surpasses the resolution that is possible using a conventional narrow probe.

Multiple aperture imaging may be used for B-mode imaging to produce high resolution spatial images of a region of interest. Using a multiple aperture imaging system for Doppler imaging may provide additional advantages in terms of the ability to detect motion in two dimensions.

As used herein the terms "ultrasound transducer" and "transducer" may carry their ordinary meanings as understood by those skilled in the art of ultrasound imaging technologies, and may refer without limitation to any single component capable of converting an electrical signal into an ultrasonic signal and/or vice versa. For example, in some embodiments, an ultrasound transducer may comprise a piezoelectric device. In some alternative embodiments, ultrasound transducers may comprise capacitive micromachined ultrasound transducers (CMUT). Transducers are often configured in arrays of multiple elements. Such arrays may have one dimension (1D), two dimensions (2D), or 1.5 dimensions (1.5D) as understood by those skilled in the art. An element of a transducer array may be the smallest discrete component of an array. For example, in the case of an array of piezoelectric transducer elements, each element may be a single piezoelectric crystal, or a single machined section of a piezoelectric crystal.

As used herein, the terms "transmit element" and "receive element" may carry their ordinary meanings as understood by those skilled in the art of ultrasound imaging technologies. The term "transmit element" may refer without limitation to an ultrasound transducer element which at least momentarily performs a transmit function in which an electrical signal is converted into an ultrasound wavefront. Similarly, the term "receive element" may refer without limitation to an ultrasound transducer element which at least momentarily performs a receive function in which an ultrasound wavefront impinging on the element is converted into an electrical signal. Transmission of ultrasound into a medium may also be referred to herein as "insonifying." An object or structure which reflects ultrasound waves may be referred to as a "reflector" or a "scatterer."

As used herein, the term "aperture" refers to a conceptual "opening" through which ultrasound signals may be sent and/or received. In actual practice, an aperture is simply a group of transducer elements that are collectively managed as a common group by imaging control electronics. For example, in some embodiments an aperture may be a physical grouping of elements which may be physically separated from elements of an adjacent aperture. For example, each of the three transducer arrays in the probe of FIG. 3 may be treated as a separate aperture. However, adjacent apertures need not necessarily be physically separated.

As used herein, the term "total aperture" refers to the total cumulative size of all imaging apertures. In other words, the term "total aperture" may refer to one or more dimensions defined by a maximum distance between the furthest-most transducer elements of any combination of send and/or receive elements used for a particular imaging cycle. Thus, the total aperture is made up of any number of sub-apertures designated as send or receive apertures for a particular cycle. In the case of a single-aperture imaging arrangement, the total aperture, sub-aperture, transmit aperture, and receive aperture will all have the same dimensions. In the case of a multiple aperture imaging arrangement, the dimensions of the total aperture includes the sum of the dimensions of all send and receive apertures and any distances between them.

As used herein, the terms "receive aperture," "insonifying aperture," and/or "transmit aperture" can carry their ordinary meanings as understood by those skilled in the art of ultrasound imaging, and may refer to an individual element, a group of elements within an array, or even entire arrays within a common housing, that perform the desired transmit or receive function from a desired physical viewpoint or aperture at a given time. In some embodiments, these various apertures may be created as physically separate components with dedicated functionality. In alternative embodiments, the functionality may be electronically designated and changed as needed. In still further embodiments, aperture functionality may involve a combination of both fixed and variable elements. In some embodiments, two apertures may be located adjacent one another on a continuous array. In still other embodiments, two apertures may overlap one another on a continuous array, such that at least one element functions as part of two separate apertures. The location, function, number of elements and physical size of an aperture may be defined dynamically in any manner needed for a particular application. Constraints on these parameters for a particular application will be discussed below and/or will be clear to the skilled artisan.

In some embodiments, the width of a receive aperture may be limited by the assumption that the speed of sound is the same for every path from a reflector to each element of the receive aperture. In a narrow enough receive aperture this simplifying assumption is acceptable. However, as receive aperture width increases, a tipping point is reached (referred to herein as the "maximum coherent aperture width") at which point the paths will typically pass though different types of material having different speeds of sound. (This is particularly true in medical imaging in which varying tissue types may have substantially different speeds of sound.) When this difference results in phase shifts approaching 180 degrees, additional receive elements beyond the maximum coherent receive aperture width will actually degrade the image rather than improve it.

Therefore, in some embodiments in order to make use of a wide probe with a total aperture width greater than the maximum coherent width, the full probe width may be physically or logically divided into multiple apertures, each of which may be limited to a width less than the maximum coherent aperture width and small enough to avoid phase cancellation of received signals. The maximum coherent width can be different for different patients and for different probe positions on the same patient. In some embodiments, a compromise (e.g., a minimum or an average optimum for a range of expected imaging scenarios) width may be established for a given probe system. In other embodiments, a multiple aperture ultrasound imaging control system may be configured with a dynamic algorithm to subdivide the available elements in multiple apertures into groups that are small enough to avoid significant phase cancellation.

As used herein, the phrase "acoustic path" refers to a path followed by an ultrasonic sound wave. In the context of multiple aperture imaging, an acoustic path originates at a transmit aperture (which may include one or more transducer elements), proceeds into the insonified material (e.g., human tissue, animal tissue, or inanimate material) to a reflector, and then returns to an element of a receive aperture. In some embodiments, an acoustic path may be described as terminating at a receive aperture rather than at an individual receive element. Such embodiments may occur when aggregating data received by multiple elements of a receive aperture. Because a multiple aperture probe may utilize any number of transmit apertures and any number of receive apertures (each of which may utilize any number of individual transducer elements), any given reflector within an insonified region may be imaged by many acoustic paths.

Thus, an acoustic path is generally a unique combination of a transmit aperture, a receive element (or a receive aperture) and a reflector. As will be described in further detail below, the geometry of a multiple aperture probe must be known in order to perform multiple aperture beamforming.

An "intra-aperture acoustic path" is an acoustic path in which a transmit aperture and the center of a receive aperture lie at the same point. For example, an acoustic path in which a single element used as a transmit aperture is also used as a receive element may be described as an intra-aperture acoustic path. Therefore, an "inter-aperture" acoustic path any acoustic path in which the transmit aperture and a center of the receive aperture do not lie at the same point.

Examples of Multiple Aperture Probes

Figure 3:
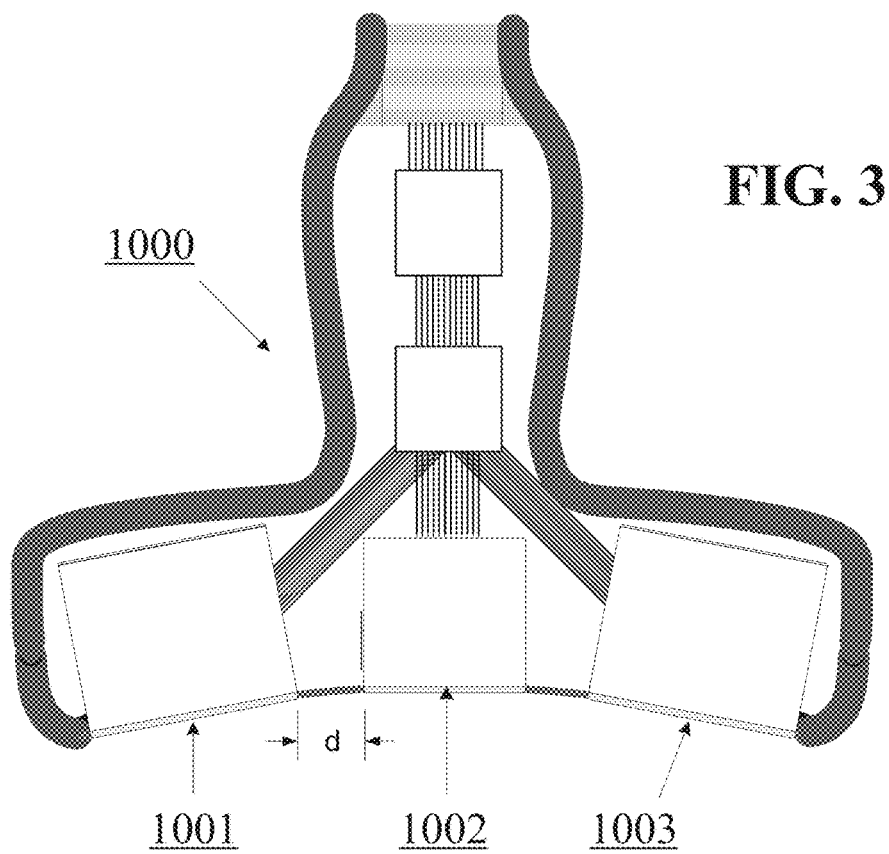
FIG. 3 is a sectional view of a multiple aperture ultrasound probe comprising multiple transducer arrays.

FIG. 3 illustrates one embodiment of a multiple aperture probe 1000 which may be used for Doppler imaging in some embodiments. The probe 1000 of FIG. 3 comprises three transducer arrays 1001, 1002, 1003, each one being a 1D, 2D or matrix transducer array. As shown, the lateral arrays 1001 and 1003 may be oriented at an angle relative to the center array 1002. In some embodiments, the angle of the lateral arrays relative to the central array can be 0 degrees but can also be any angle greater than 0 degrees. In one embodiment, a pair of lateral arrays 1001 and 1003 may be arranged at angles of about 30 degrees below a horizontal central array 1002. In some embodiments, the probe 1000 of FIG. 3 may have a total width substantially wider than 2 cm, and in some embodiments 10 cm or greater.

In some embodiments as shown in FIG. 1, a probe 1000 may comprise separate transducer arrays 1001, 1002, 1003 which may be physically separated from one another. For example, in FIG. 1, a distance 'd' physically separates the left array 1001 from the center array 1002. Distance 'd' can be the minimum distance between transducer elements on aperture 1001 and transducer elements on aperture 1002. In some embodiments, the distance 'd' may be zero or as large as may be desired for a particular application. In alternative embodiments, a distance between apertures may be as large as possible to increase the lateral resolution of the multi-aperture imaging system within the constraints of a particular application. In some embodiments, probes may be constructed to provide an adjustable distance or angle between adjacent transducer arrays. Such adjustability may provide flexibility for imaging a wide range of anatomic structures.

Figure 4:
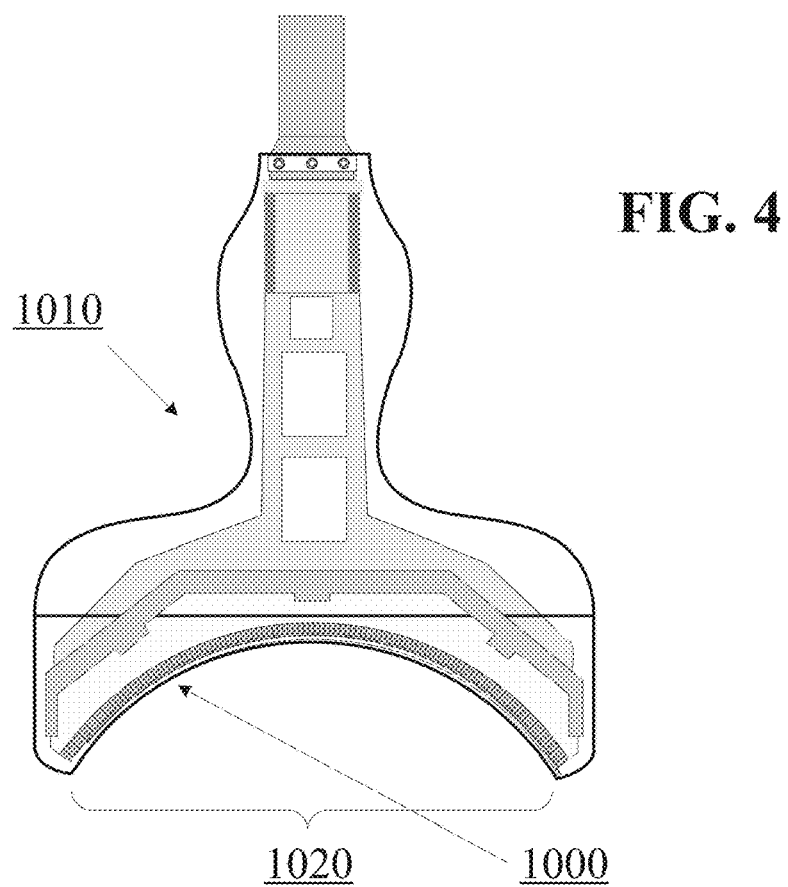
FIG. 4 is a sectional view of an ultrasound probe having a single continuous curved 1D, 1.5D, 2D or CMUT transducer array.

FIG. 4 illustrates an alternative embodiment of a multiple aperture probe 1010 which may be used for Doppler imaging in some embodiments. The probe of FIG. 4 comprises a single continuous 1D, 1.5D, 2D or CMUT transducer array 1012 having a total width 1020 substantially wider than a maximum coherent width for any anticipated imaging scenario. For example, in some embodiments, the total width 1020 of the array 1012 of the probe 1010 in FIG. 4 may be greater than about 2 cm, and in some embodiments may be 10 cm or greater. In the embodiment of FIG. 2, any number of apertures may be dynamically assigned as needed. The array 1012 is shown with a symmetrical continuous concave curve, however in alternative embodiments, the array 1012 may have any other symmetrical or asymmetrical concave or planar shape as desired.

In some embodiments, a distance and orientation between adjacent apertures may be fixed relative to one another, such as by use of a rigid housing. In alternative embodiments, distances and orientations of apertures relative to one another may be variable, such as with a movable linkage. In alternative embodiments, the systems and methods below may be used with any multiple aperture probe as desired. In still further embodiments any of the multiple aperture ultrasound probe configuration described in Applicants' previous applications referenced above may be used in combination with the various embodiments of Doppler imaging systems and methods described herein.

In some embodiments, multiple aperture ultrasound probes and imaging processes may be used in combination with a scanline-based phased array transmission system. In other embodiments, multiple aperture ultrasound probes and imaging processes are uniquely suited to benefiting from a completely different transmit waveform.

Introduction to Ping-Based Imaging

In contrast to conventional scanline-based phased array ultrasound imaging systems, some embodiments of multiple aperture ultrasound imaging systems may use point source transmission during the transmit pulse. An ultrasound wavefront transmitted from a point source (also referred to herein as a "ping") illuminates the entire region of interest with each circular or spherical wavefront. Echoes received from a single ping received by a single receive transducer element may be beamformed to form a complete image of the insonified region of interest. Combining data and images from multiple receive transducers across a wide probe, and combining data from multiple pings, very high resolution images may be obtained. Moreover, such a system allows for imaging at a very high frame rate, since the frame rate is limited only by the ping repetition frequency—i.e., the inverse of the round-trip travel time of a transmitted wavefront travelling between a transmit transducer element, a maximum-depth reflector, and a furthest receive transducer element. In some embodiments, the frame rate of a ping-based imaging system may be equal to the ping repetition frequency alone. In other embodiments, if it is desired to form a frame from more than one ping, the frame rate of a ping-based imaging system may be equal to the ping repetition frequency divided by the number of pings per frame.

As used herein the terms "point source transmission" and "ping" may refer to an introduction of transmitted ultrasound energy into a medium from a single spatial location. This may be accomplished using a single ultrasound transducer element or combination of adjacent transducer elements transmitting together. A single transmission from said element(s) may approximate a uniform spherical wave front, or in the case of imaging a 2D slice it creates a uniform circular wave front within the 2D slice. In some cases, a single transmission of a circular or spherical wave front from a point source transmit aperture may be referred to herein as a "ping" or a "point source pulse" or an "unfocused pulse."

Point source transmission differs in its spatial characteristics from a scanline-based "phased array transmission" or a "directed pulse transmission" which focuses energy in a particular direction (along a scanline) from the transducer element array. Phased array transmission manipulates the phase of a group of transducer elements in sequence so as to strengthen or steer an insonifying wave to a specific region of interest.

In some embodiments, multiple aperture imaging using a series of transmit pings may operate by transmitting a point-source ping from a first transmit aperture and receiving echoes of the transmitted ping with elements of two or more receive apertures. A complete image may be formed by triangulating the position of reflectors based on delay times between transmission and receiving echoes. As a result, each receive aperture may form a complete image from echoes of each transmitted ping. In some embodiments, a single time domain frame may be formed by combining images formed from echoes received at two or more receive apertures from a single transmitted ping. In other embodiments, a single time domain frame may be formed by combining images formed from echoes received at one or more receive apertures from two or more transmitted pings. In some such embodiments, the multiple transmitted pings may originate from different transmit apertures.

Embodiments of Ping-Based Beamforming

Beamforming is generally understood to be a process by which imaging signals received at multiple discrete receptors are combined to form a complete coherent image. The process of ping-based beamforming is consistent with this understanding. Embodiments of ping-based beamforming generally involve determining the position of reflectors corresponding to portions of received echo data based on the path along which an ultrasound signal may have traveled, an assumed-constant speed of sound and the elapsed time between a transmit ping and the time at which an echo is received. In other words, ping-based imaging involves a calculation of distance based on an assumed speed and a measured time. Once such a distance has been calculated, it is possible to triangulate the possible positions of any given reflector. This distance calculation is made possible with accurate information about the relative positions of transmit and receive transducer elements. (As discussed in Applicant's previous applications referenced above, a multiple aperture probe may be calibrated to determine the acoustic position of each transducer element to at least a desired degree of accuracy.) In some embodiments, ping-based beamforming may be referred to as "dynamic beamforming."

A dynamic beamformer may be used to determine a location and an intensity for an image pixel corresponding to each of the echoes resulting from each transmitted ping. When transmitting a ping signal, no beamforming need be applied to the transmitted waveform, but dynamic beamforming may be used to combine the echoes received with the plurality of receive transducers to form pixel data.

Figure 5:
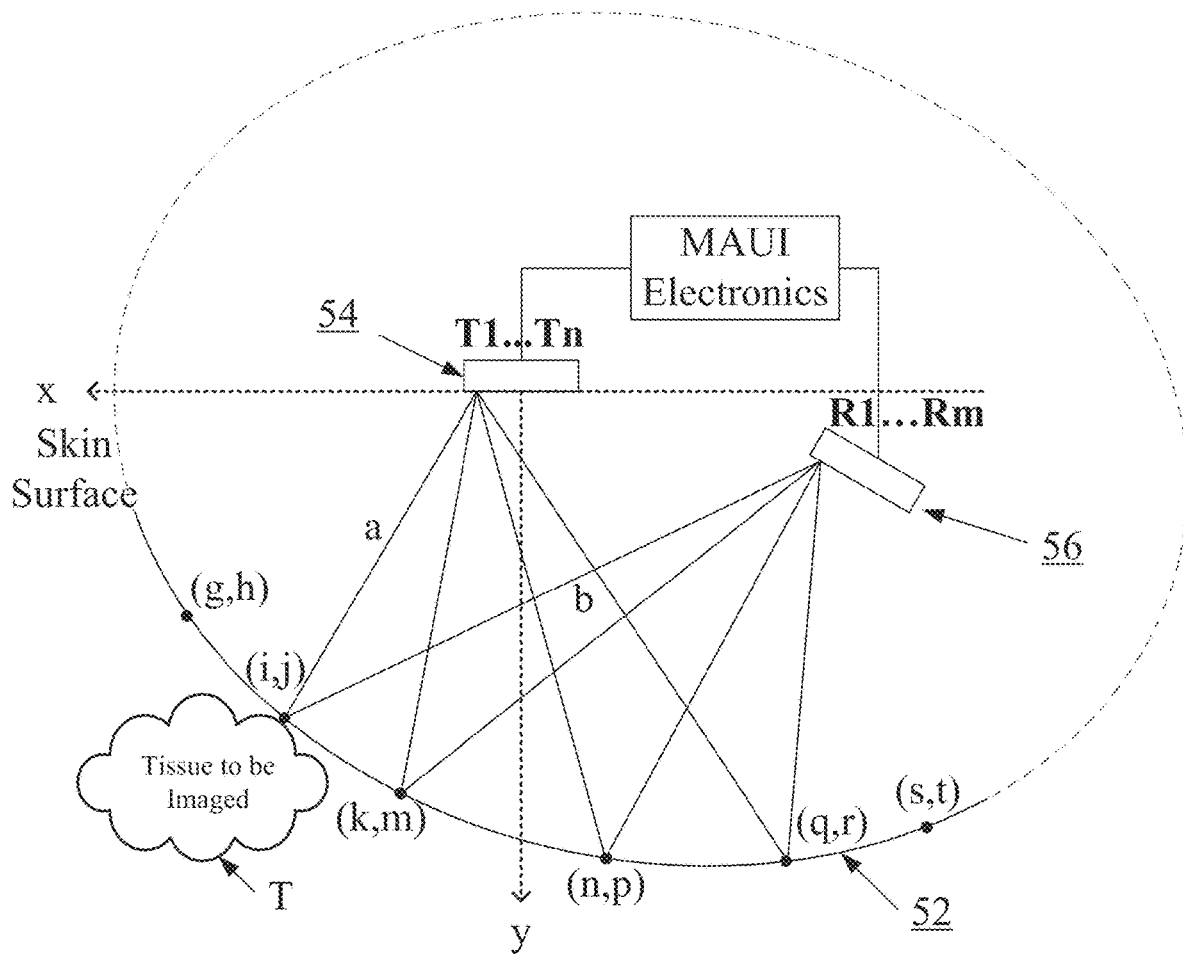
FIG. 5 is a schematic illustration of an embodiment of a ping-based beamforming technique.
Figure 6:
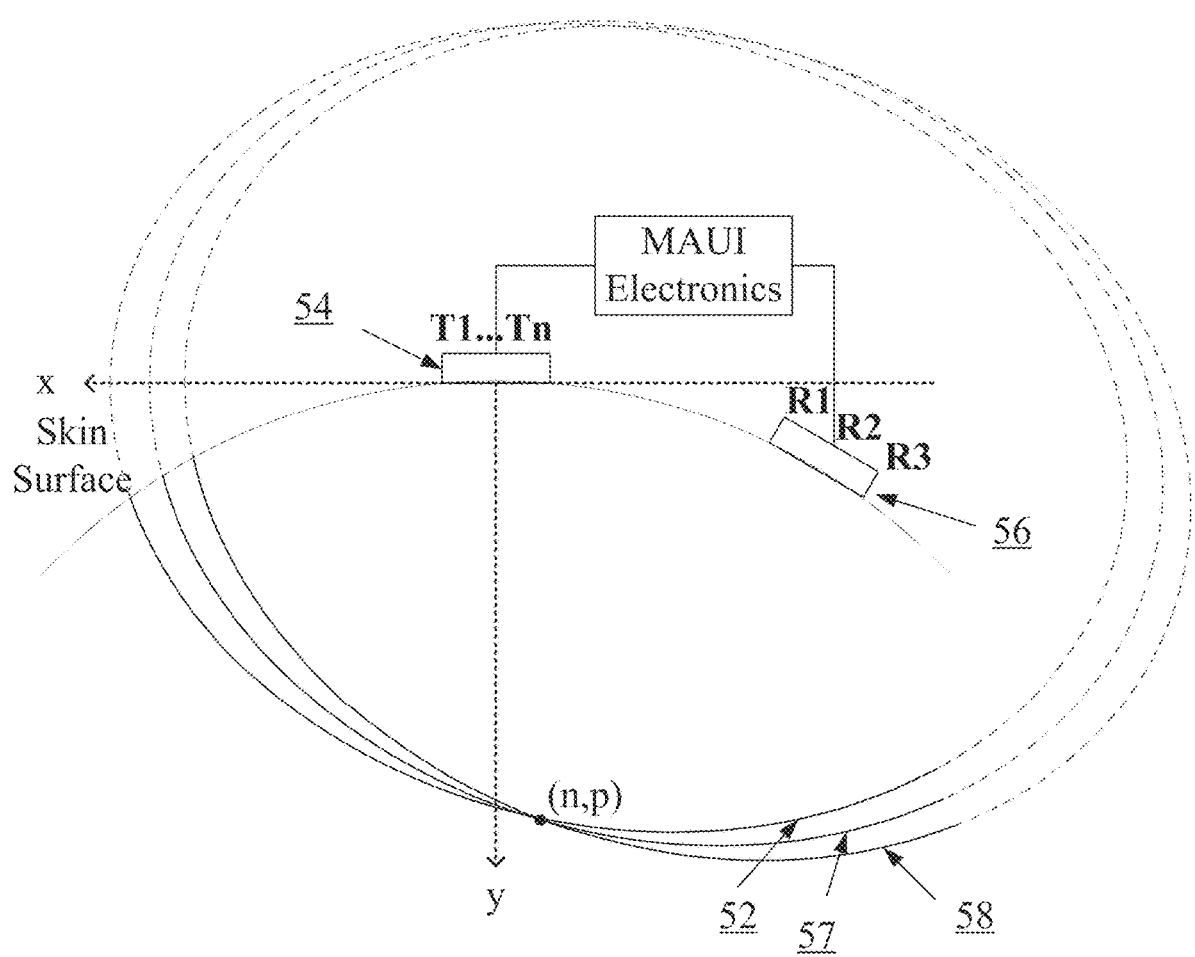
FIG. 6 is a second schematic illustration of an embodiment of a ping-based beamforming technique.

As used herein, dynamic beamforming refers to the fact that a beamformer's focus may be continuously changed to focus at each pixel position as that pixel is being imaged. In some embodiments, a dynamic beamformer may plot the locus of every echo from the transmitter to each receive transducer element at each instant of time. The locus of a single reflector (e.g., point (n,p) in FIG. 5) will lie along an ellipse 52 in FIG. 5 with a first focus at the position of the transmit transducer element(s) 54 and the second focus at the position of the receive transducer element 56. Although several other possible reflectors lie along the same ellipse (as indicated by reflectors (g,h), (i,j), (k,m), etc.), echoes of the same reflector (n,p) will also be received by each of the other receive transducer elements of a receive aperture. The slightly different positions of each receive transducer element (R1, R2, R3) means that each receive element will have a slightly different ellipse for reflector (n,p) as illustrated in FIG. 6. Accumulating the results by coherently summing the ellipses (e.g., 52, 57, 58) for all elements of a common receive aperture will indicate an intersection of all ellipses of a receive aperture, thereby converging towards a point at which to display a pixel representing the reflector (n,p). The echo amplitudes received by any number of receive elements may thereby be combined into each pixel value. Such a system may also be referred to as an accumulator. In other embodiments the computation can be organized differently to arrive at substantially the same image.

The image quality may be further improved by combining images formed by the beamformer from one or more subsequent transmitted pings. Still further improvements to image quality may be obtained by combining images formed by more than one receive aperture. An important consideration is whether the summation of images from different pings or receive apertures should be coherent summation (phase sensitive) or incoherent summation (summing magnitude of the signals without phase information). In some embodiments, coherent (phase sensitive) summation may be used to combine echo data received by transducer elements located on a common receive aperture resulting from one or more pings. In some embodiments, incoherent summation may be used to combine echo data or image data received by receive apertures that could possibly contain cancelling phase data. Such may be the case with receive apertures that have a combined total aperture that is greater than a maximum coherent aperture width for a given imaging target.

In some embodiments, a first set of images may be obtained using in-phase data, and a second set of images may be obtained from quadrature data.

Various embodiments of such a dynamic beamformer used in B-mode imaging are described in Applicant's prior applications, including U.S. Pat. No. 8,007,439 and U.S. Patent Application Publication No. 2011-0201933-A1.

Introduction to Ping-Based Doppler

In contrast to conventional scanline-based phased array ultrasound imaging systems, some embodiments of multiple aperture ultrasound imaging systems may use point source transmission during the transmit pulse. An ultrasound wavefront transmitted from a point source (also referred to herein as a "ping") illuminates the entire region of interest with a circular or spherical wavefront. As a result, there is no need to establish a limited region of interest for Doppler measurement (e.g., a "range gate" as such limited regions are commonly known in the art) prior to transmit with a ping-based imaging system because Doppler signals may be detected from any point in the imaging field of view. As a result, some embodiments of the systems and methods described herein may be configured to cycle through and individually seek motion information from a plurality of "test segments" within an entire insonified region of interest in order to determine which of such test segments include moving reflectors. This significant advantage applies to both one-dimensional Doppler signals (i.e., flow towards or away from a probe or array) and to Vector Doppler which utilizes more than one transducer array to detect two-dimensional motion vectors within the image plane. When using Vector Doppler (i.e., Doppler imaging using laterally spaced arrays or array sections) in combination with ping transmission, reflectors can be designated along an axis that has any orientation within the image plane. An axis may even be tangential to the multiple aperture transducer, and is not restricted to being aligned with the transducer. The multiple aperture probe need only illuminate the area of interest, as flow can be calculated in all directions.

In various embodiments, a multiple aperture ultrasound imaging system may be configured to perform B-mode imaging with a multiple aperture probe using unfocused broad wavefront pulses, such as a semicircular or spherical wavefront pulse. Such broad wavefront pulses may be formed by transmitting a short-duration ultrasound wavefront signal from a point-source element (or group of elements). In such embodiments, it may also be desirable to use broad wavefront transmit beams for detecting motion of imaged objects or substances using Doppler techniques. Advantages to such a system include the lack of a need for a transmit beamformer and the potential for a common receive beamformer for both Doppler and B-mode imaging.

Additionally, range gates need not be pre-assigned in a narrow sector. Instead, every pixel in the image may be individually tested as a "test segment". Furthermore, in some embodiments performing Doppler imaging with a multiple aperture probe having at least two apertures means that blood flow velocity may be detected in all directions. A multiple aperture probe having three or more apertures may provide further improvements.

Embodiments of Ping-Based Doppler Transmit Waveforms

Figure 7:
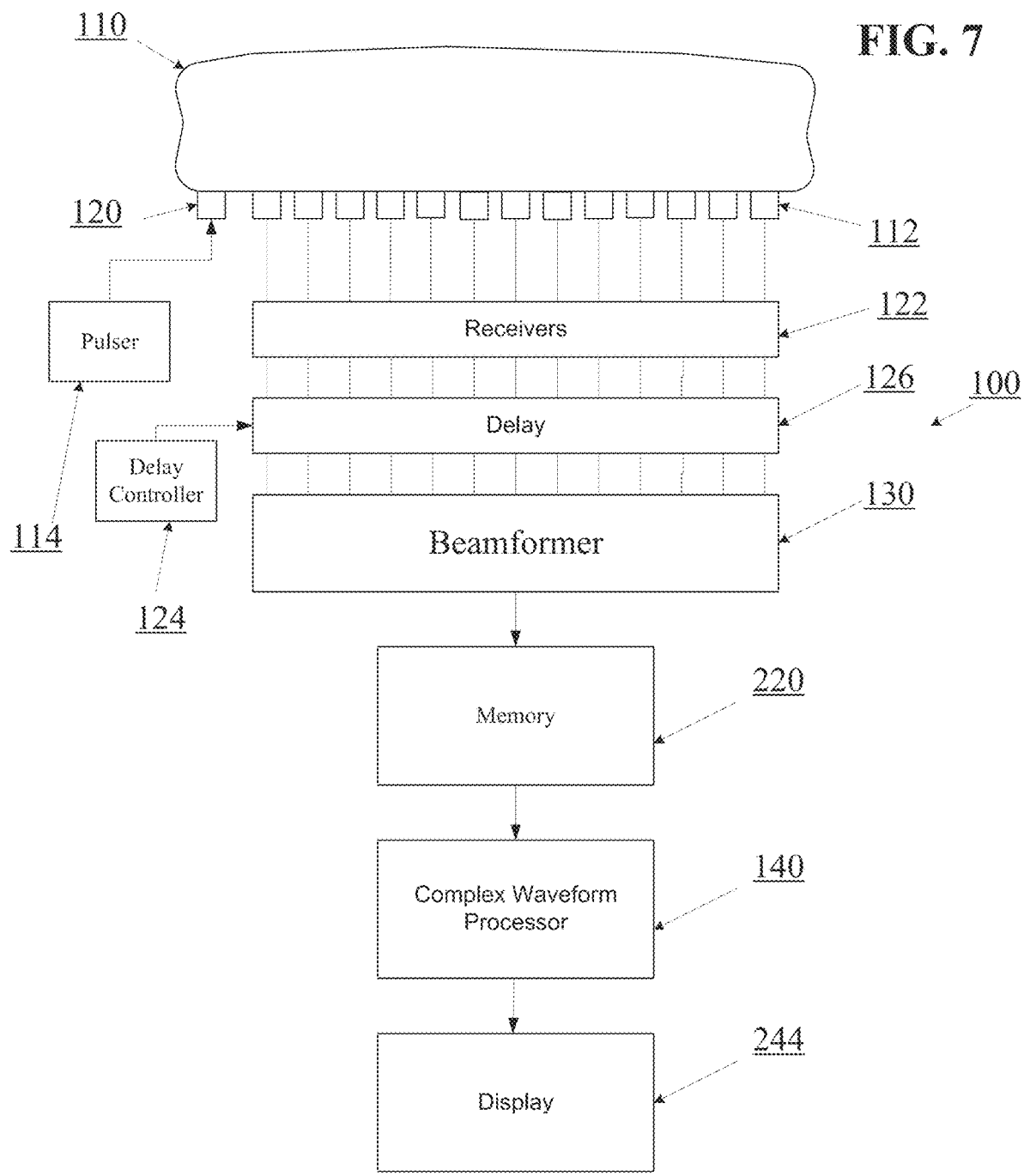
FIG. 7 is a block diagram illustrating an embodiment of a Doppler sub-system.

FIG. 7 provides a block diagram illustrating an embodiment of a ping-based Doppler processing sub-system 100 for measuring motion within an object 110. The Doppler processing sub-system 100 may be independent of, or integrated into a broader ultrasound imaging system. In some embodiments, the transmit transducer element(s) 120 and the receive transducer elements 112 controlled by the ping-based Doppler sub-system 100 may be a sub-set of all of the elements of an ultrasound probe (e.g., any of FIG. 3, 3, 8 or 10-13 or any other multiple aperture probe configuration). Echo signals received by the receive transducer elements 112 may be transmitted to channel-specific receive electronics 122 which may include various analog-to-digital and filtering electronics. In some embodiments, the ping-based Doppler sub-system 100 may be configured to control all of the available transducer elements of a probe. In some embodiments, the transmit element 120 may be a single transducer element dedicated for a Doppler transmit function, but in other embodiments, the transmit element 120 may comprise any number of transducer elements of a probe that may be instantaneously designated and operated as a Doppler transmit element. A delay controller 124 may be provided to apply channel-specific delays 126 to received echo signals for storing in-phase and quadrature echo signals as will be described in further detail below. Memory 220 and Display 244 devices such as those described in more detail below may also be included.

The Doppler sub-system 100 of FIG. 7 may also include a (software or hardware) beamformer configured to perform a ping-based beamforming process as will be described in further detail below. A complex waveform processor 140 may be used to perform complex processing of in-phase and quadrature echo signals in order to detect Doppler shift frequencies and/or to determine a direction of motion of Doppler signals.

Figure 8:
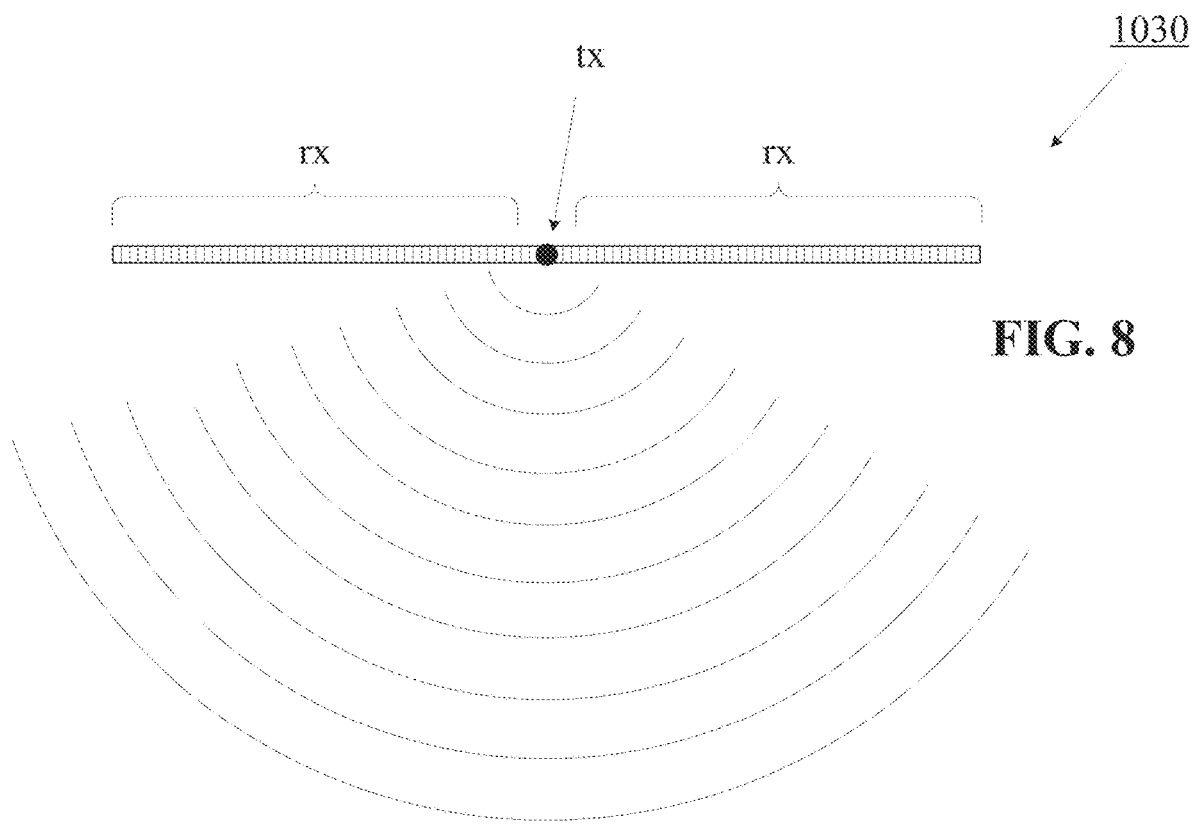
FIG. 8 is a schematic illustration of an ultrasound transducer array comprising many receive elements but only a single transmit element.

FIG. 8 illustrates an embodiment of a probe 1030 comprising many receive elements 'rx' but a relatively small transmit aperture 'tx' (which may consist of a single transducer element or may include two, three, four, five or more elements in combination) used to transmit an unfocused point source pulse signal (aka a "ping"). In some embodiments, the transmit aperture may include one or more elements of a standard array or it may be a special transducer designed to withstand larger voltage swings and to be more efficient as a transmitter than as a receiver. In some embodiments, the receive elements 'rx' may be used in the receive-only mode and therefore don't require the expense and suffer the attenuation of a transmit/receive switch on each element.

In some embodiments a probe 1030 such as that schematically illustrated in FIG. 8 may be a "single aperture probe" in which the total aperture is designed to be narrower than the maximum coherent width for the majority of imaging scenarios for which the probe is designed. Alternatively, the schematic of FIG. 8 may also represent any single aperture of a multiple aperture probe.

In use, a ping-based Doppler sub-system (e.g., as shown in FIG. 7) may control a probe, such as that shown in FIG. 8 to repeatedly transmit pings from the transmit transducer 'tx' at a high ping repetition rate and the echoes received by the receive transducers 'rx' may be digitized by the Doppler sub-system 100. In some embodiments, a maximum theoretical ping repetition rate may be limited by the speed of sound in the target tissue and a target depth of a region of interest (accounting for any attenuation). For example, a maximum ping repetition rate is preferably slow enough such that a first transmit wavefront travels from the transmit transducer, is reflected by objects in the region of interest, and reaches the receive transducers before a second wavefront is transmitted. However, the ping repetition rate need not be any slower than this round-trip travel time. In some embodiments, a further margin of safety may be added onto the time between pulses to avoid overlapping pulses at the receive transducers. In various embodiments, ping repetition rates from about 2,000 Hz to about 8,000 Hz or more may be supported. In some embodiments a ping repetition rate of about 2500 Hz may be used.

The system of FIG. 7 may further includes a pulser configured to produce Doppler transmit waveforms. In various embodiments, ultrasound pings transmitted for the purpose of evaluating motion using Doppler techniques may have different characteristics than pings (or other ultrasound signals) transmitted for imaging (e.g., B-mode) purposes. In some embodiments, waveforms to be used in Doppler imaging may be transmit at a lower frequency than the frequency of waveforms transmitted for B-mode imaging used for the same region of interest. For example, if a B-mode image is obtained using ultrasound signals transmitted at a frequency of 3 MHz, a corresponding Doppler color flow image (e.g., to be overlaid on the B-mode image) may be obtained using ultrasound waveforms transmitted at 2 MHZ. As is well known in the art, the highest Doppler frequency that can be detected without aliasing is PRF/2. In the context of ping-based Doppler, this means that the maximum Doppler frequency detectable without aliasing is half the transmitted Doppler ping frequency. Therefore transmitting Doppler pings with a center frequency that is lower than that for B-mode imaging may reduce the occurrence of aliasing of the Doppler signals.

Ultrasound pings for Doppler imaging may also be transmitted with a longer pulse length (i.e., more cycles) than pings transmitted for B-mode imaging. A longer pulse length causes the wavefront to persist at a particular test segment for a sufficiently long time so that a Doppler shift may be detected in the returned echoes. The pulse length of such Doppler transmit pings may be measured in cycles. In various embodiments, depending on characteristics of the medium being imaged, the frequency of transmit signals, the depth of a region of interest and other factors, a Doppler ping may have a pulse length of a single cycle up to tens or dozens of cycles or more. In some particular embodiments, a Doppler ping may have a pulse length of between about 10 cycles and about 32 cycles. In a few specific examples, a Doppler ping may have a pulse length of about 10 cycles, 12 cycles, 13 cycles, 14 cycles, 15 cycles, 16 cycles, 17 cycles, 18 cycles, 19 cycles or 20 cycles.

An increased pulse length may result in increased "Doppler resolution" (i.e., the quality of measurements of the velocity of moving reflectors), but a longer pulse length will also typically result in decreased "spatial resolution" (i.e., the quality of information describing the position of moving reflectors). As a result, any selection of a pulse length for a Doppler transmit ping will involve balancing these two competing factors. In some embodiments, a user interface control may be provided to allow a user to increase or decrease a transmit pulse length. Adjustments to pulse length may be performed manually based on a user's assessment of factors such as the material, size or density of an object to be imaged, a desired imaging depth, or a preference for motion-detection accuracy vs. moving reflector position accuracy, or other relevant factors. In other embodiments, an ultrasound imaging system may automatically adjust a transmit pulse length based on an automatic assessment or manual entry of information relating to such factors.

In some embodiments, an ultrasound system may be configured to alternate between transmitting Doppler signals and B-mode imaging signals. In such embodiments, after a long Doppler ping is transmitted from a single transmit aperture, one or more B-mode imaging signals may be transmitted from one or more B-mode imaging transmit apertures. In some embodiments, the B-mode imaging transmit signals, which may comprise one or more pings with a shorter pulse length and a higher frequency than the Doppler ping, may be transmitted from the same transmit aperture as the Doppler signals, or from one or more different transmit aperture(s). In other embodiments, a Doppler imaging system may be configured to transmit a second Doppler ping, or a series of Doppler pings from the same transmit aperture as the first Doppler ping. In still other embodiments, a Doppler imaging system may be configured to transmit a second Doppler ping from a second transmit aperture after transmitting a first Doppler ping from a first transmit aperture. In still further embodiments, any number of transmit apertures may be used to transmit Doppler pings. In most embodiments, a complete Doppler ping will typically be transmitted from one transmit aperture before proceeding to transmit further Doppler pings from other transmit apertures.

In some embodiments, a Doppler ping may also include a preamble and/or a postamble signal which may be used by a receive system to recognize the beginning and/or ending (respectively) of the Doppler ping signal. Such preamble and/or postamble signals may include any signal shape as desired.

Embodiments of Receiving and Storing Ping-Based Doppler Echo Data

In various embodiments, the echoes received by the receive apertures may be digitized and stored in a memory device (e.g., using a system such as that described in further detail below). In some embodiments, echo data received from a Doppler ping may be stored in two data sets, referred to herein as an in-phase data set and a quadrature data set. In-phase data represents the received echo signals with zero delay. Quadrature data represents the same echo signals, but at a delay of about one-quarter of the center frequency period of the transmit waveform relative to the in-phase data. As described in further detail below, in-phase and quadrature data may be analyzed and compared to determine the direction of any Doppler shift.

As described in further detail below with reference to FIG. 19, echo data may be stored in a separate data stream for each receive transducer element. In some embodiments, two data streams (e.g., in-phase and quadrature) or more may be stored for each transducer element.

As used herein, the term "test segment" refers to a discrete portion of received Doppler echo data under examination. The concept of a test segment is similar to, but far more inclusive than the concept of a Doppler range gate used in conventional scanline-based Doppler imaging. In scanline-based Doppler imaging, available test segments are limited to only those sections of the insonified object that have been predefined as Doppler range gates prior to transmitting and receiving ultrasound signals. In such conventional scanline-based ultrasound imaging systems, only data along the scanline is significantly insonified at any one time. Thus, in scanline-based systems, a Doppler gate must be made up of a region that lies along the scanline between a targeted minimum and maximum depth.

By contrast, in ping-based Doppler imaging systems utilizing a broad wavefront or point source transmit pulse (e.g., a ping), the entire image plane is insonified with each transmitted ping, and as a result, any (or every) pixel in the image plane may be analyzed as a separate test segment without the need to predefine a narrow region in which to test for Doppler frequencies. In other embodiments, test segments may be defined as a group of adjacent pixels. In some embodiments, the size of one or more test segments may be selected by a user through an appropriate user interface device such as a dial, slider, numeric keypad, touch screen gesture, etc.

Using a dynamic beamforming technique as described above, echoes of a Doppler ping received by all elements of a receive aperture may be combined to determine a position for each reflector (represented by one or more pixels). The reflectors so positioned may then be arranged into test segments to be evaluated for Doppler frequency detection. In other embodiments, echo data may be arranged into test segments based solely on time-of-arrival of echo data.

Embodiments of Doppler Frequency Detection

Doppler shift frequencies may be identified by dividing echoes from a single Doppler ping received by a single transducer element into a number of samples. In some embodiments, an echo signal may be divided into samples such that each sample is approximately the size of a single cycle of the transmit frequency. For example, if a Doppler transmit ping has a pulse length of 16 cycles, echoes received from such a Doppler ping may be divided into 16 equal-length samples for Doppler frequency detection. Samples may then be analyzed to determine whether the frequency of the received echoes have a higher or lower frequency than the frequency of the corresponding transmitted Doppler ping. Echoes with higher or lower frequencies than the corresponding transmitted Doppler ping indicate moving reflectors. If a reflector is not moving, the amplitude of all samples of an echo signal from that reflector will be substantially equal to one another. If the reflector is moving, the amplitude of the samples may be expected to vary at the Doppler frequency. In some embodiments, detection of Doppler frequencies may be further aided by dividing a received echo signal into in-phase and quadrature data streams as described above. This is further illustrated with reference to FIGS. 9A and 9B.

Figure 9A:
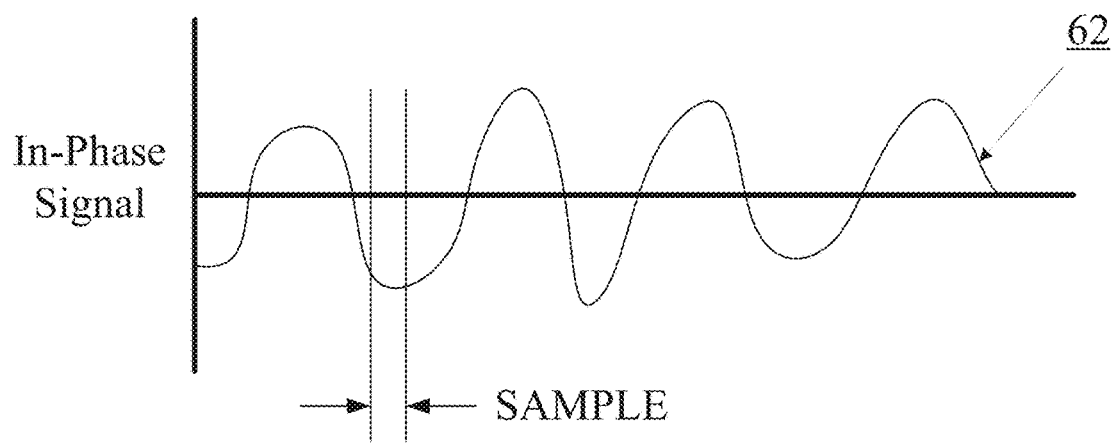
FIG. 9A is an amplitude vs. time graph of in-phase echoes received from a Doppler ping.
Figure 9B:
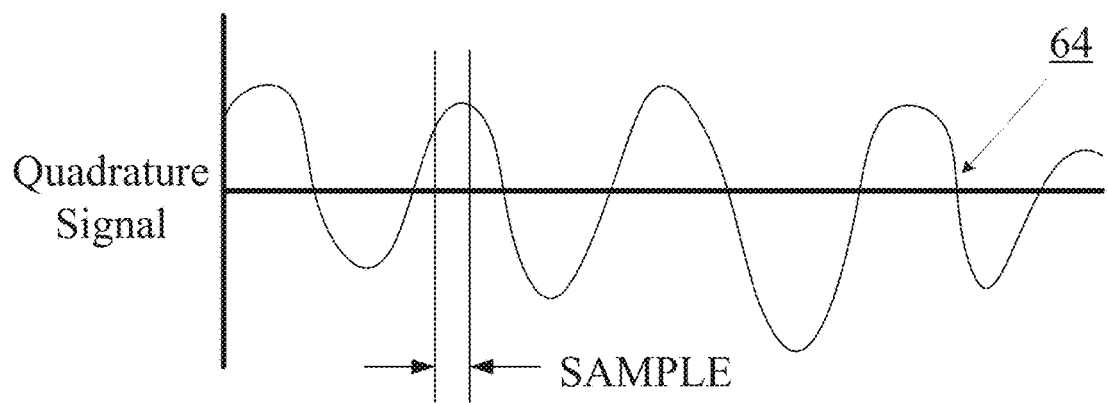
FIG. 9B is an amplitude vs. time graph of quadrature echoes received from a Doppler ping.

FIG. 9A illustrates an examples of a waveform 62 of in-phase echo data for a single test segment obtained from a Doppler ping, and FIG. 9B illustrates a corresponding waveform 64 of quadrature echo data for the same test segment obtained from the same Doppler ping. If the test segment in question were positioned at a point of zero motion, the waveforms of FIGS. 9A and 9B would have constant amplitudes and would have a frequency substantially equal to the frequency of the transmitted Doppler ping (plus the effects of inevitable noise). In fact, the waveforms of FIGS. 9A and 9B represent a point in motion and are thus samples of the corresponding Doppler frequency. Thus, by comparing the detected frequency of the received echo signal with the known frequency of the transmitted ping signal, a Doppler shift may be detected. With two such signals with approximately 90 degrees of phase shift between them (i.e., an in-phase signal and a quadrature signal), it is possible to determine whether the motion is towards or away from the transducer probe. In alternative embodiments, any other known method of detecting Doppler frequencies from a received waveform may also be used.

Once Doppler shift frequency is detected for a given moving reflector, the speed associated with the detected Doppler frequency may be calculated directly based on the timing of received Doppler echoes and known information such as a speed of sound ('c') in the imaged medium. For example, in some embodiments a technique known as time domain correlation (TDC) may be used in which reflector displacement ($\Delta x$) is determined by taking half the product of the speed of sound ('c') and the detected time shift ($\Delta t$, corresponding to the Doppler frequency shift).

$$\Delta x = c * \Delta t$$

The speed of the moving reflector (Vr) is simply the displacement ($\Delta x$) divided by the period between consecutive cycles of the transmitted waveform (PP):

$$Vr = \Delta x / PP$$

In various alternative embodiments, any other known method of quantifying reflector speed based on a detected Doppler frequency may also be used.

In addition to the scalar speed of a reflector, the vector direction of motion may also be determined with varying degrees of accuracy, depending on the type of analysis being used, processing power available, the type of probe being used, and other factors. In general, motion may be detected one-dimensionally or multi-dimensionally.

Embodiments of One-Dimensional Doppler Motion Detection

In some embodiments, such processing may be accomplished by performing a Fast Fourier Transform on a complex (real and imaginary) combination of an in-phase waveform 62 and a quadrature waveform 64 such as those illustrated in FIGS. 9A and 9B. The result of such an operation will yield a complex vector of N elements. The complex elements may then be converted to amplitude or a power spectrum may be computed. Half of the elements correspond to positive Doppler shifts (motion towards the probe) and the other half correspond to negative shifts (motion away from the probe). In alternative embodiments, such processing may be accomplished with an infinite impulse response (IIR) filter of three or more frames sampled at the transmitted Doppler ping frequency. In further embodiments, any other quadrature detection method or any other known method may be used to make a one-dimensional determination of the direction of moving reflectors based on detected Doppler frequencies. In some embodiments, the results of such Doppler processing may be displayed to a clinician and may also be provided with an audio output as well. In some embodiments, Doppler data may be displayed as an overlay to a B-mode scan.

In some embodiments, as described above with reference to FIG. 2, prior to performing any beamforming 20, raw un-beamformed echo data received by each element of a receive aperture following a transmitted Doppler ping may be analyzed to detect Doppler frequency shifts 24 indicating moving reflectors. In such embodiments, "test segments" may be defined and selected 19 based on relative timing of echoes received by a receive element rather than based on the position of reflectors (determined by beamforming) as in the above embodiments. In such embodiments, Doppler frequencies may be detected 24 in substantially the same manner described above, but rather than defining test segments based on reflector position, test segments may be defined by the timing of echo signals received by each receive element.

In some such embodiments, once motion is detected 24 in one or more sections of echo data, those echoes indicating moving reflectors may then be beamformed 20 to determine locations for pixels representing those moving reflectors. Through such beamforming (e.g., using a dynamic beamforming process such as that described above), the positions of moving reflectors in the Doppler echo data may be determined. Doppler echo data received at all receive elements of a single receive aperture may be combined by coherent summation in order to improve lateral resolution of resulting position information.

In some embodiments, portions of the Doppler echo data set that indicate no motion, or those portions that indicate motion at speeds below a threshold value may be ignored when beamforming to locate pixel positions representing moving pixels in an image (or an image layer) to be displayed. In this way, only Doppler echo data resulting from reflectors moving faster than a threshold value may be used in building a Doppler image.

In some embodiments, an automated heuristic analysis of a B-mode image may be used to improve the spatial resolution of Doppler information to be included in a final Doppler image (or a Doppler image layer of a composite image). For example, a B-mode image may be evaluated to identify blood vessels (e.g., using a process such as that described in U.S. Pat. No. 8,105,239). With such information, an imaging system may be configured to produce an image indicating motion in only those regions identified as blood vessels. Similar methods may be applied in other medical or non-medical applications.

In some embodiments, detected movement may be indicated as a color on a display. In embodiments in which detected motion is one-dimensional (i.e., towards or away from a probe), motion in one direction (e.g., towards the probe) may be indicated in one color such as red, and motion in the opposite direction (e.g., away from the probe) may be indicated in another color, such as blue. Varying Doppler frequencies may be indicated by varying intensities of the two chosen colors. Such a colored Doppler image may then be overlaid with a B-mode image in order to provide context to the Doppler motion information. In other embodiments, a Doppler image may be displayed independently. Using one-dimensional ping-based Doppler methods, motion at any point within a B-mode image may be displayed without the need to specifically define a Doppler region of interest (or test segment) in advance. This is because a Doppler ping will insonify the entire region of interest as defined by the extent of a corresponding B-mode image.

Embodiments of Multi-Dimensional Doppler Motion Detection

By using more than one receive aperture or more than one transmit element, components of flow aligned along more than one axis may also be detected. In such embodiments, components of flow along different axes can be combined to find total speed and direction of flow for each gate or pixel. For example with reference to FIG. 8, the receive elements 'rx' on the left of the transmit aperture 'tx' of the probe 1030 may be processed as one receive aperture (e.g., using one of the one-dimensional processes described above), and the receive elements 'rx' on the right of the transmit aperture 'tx' may be processed as a separate receive aperture. In this case, the direction of maximum flow sensitivity would be slightly different for the right-side aperture as compared with the left-side aperture. In some embodiments, this difference in directional sensitivity may be exploited to infer the total flow and direction of the target object (e.g., blood in an artery).

Figure 10:
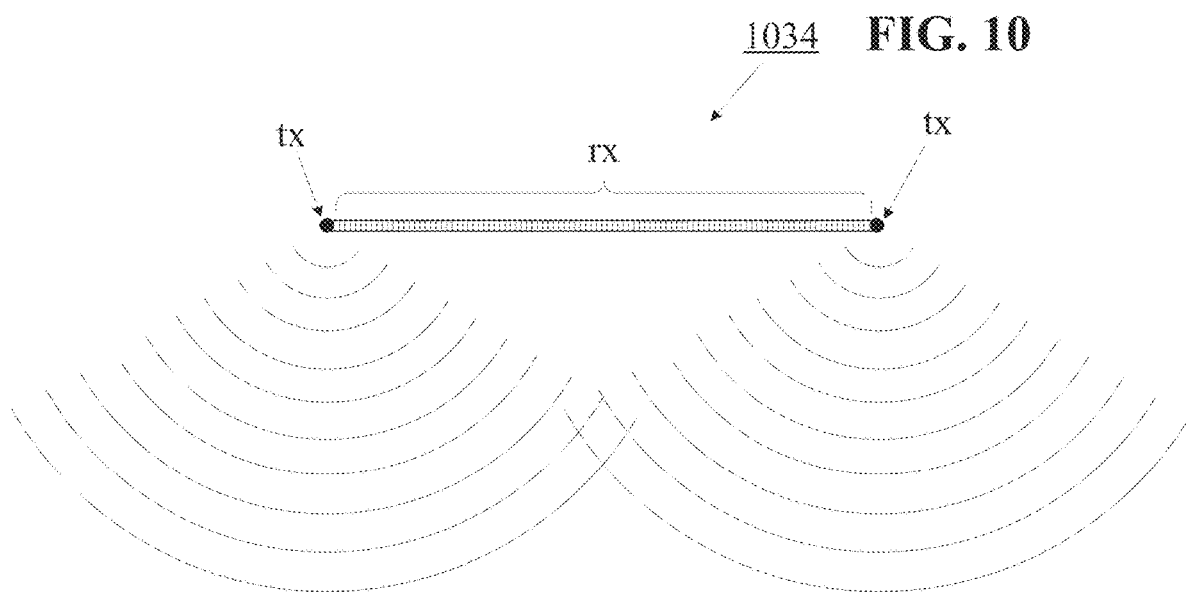
FIG. 10 is a schematic illustration of an ultrasound probe comprising an array of many receive elements with a transmit element on either end.
Figure 11:
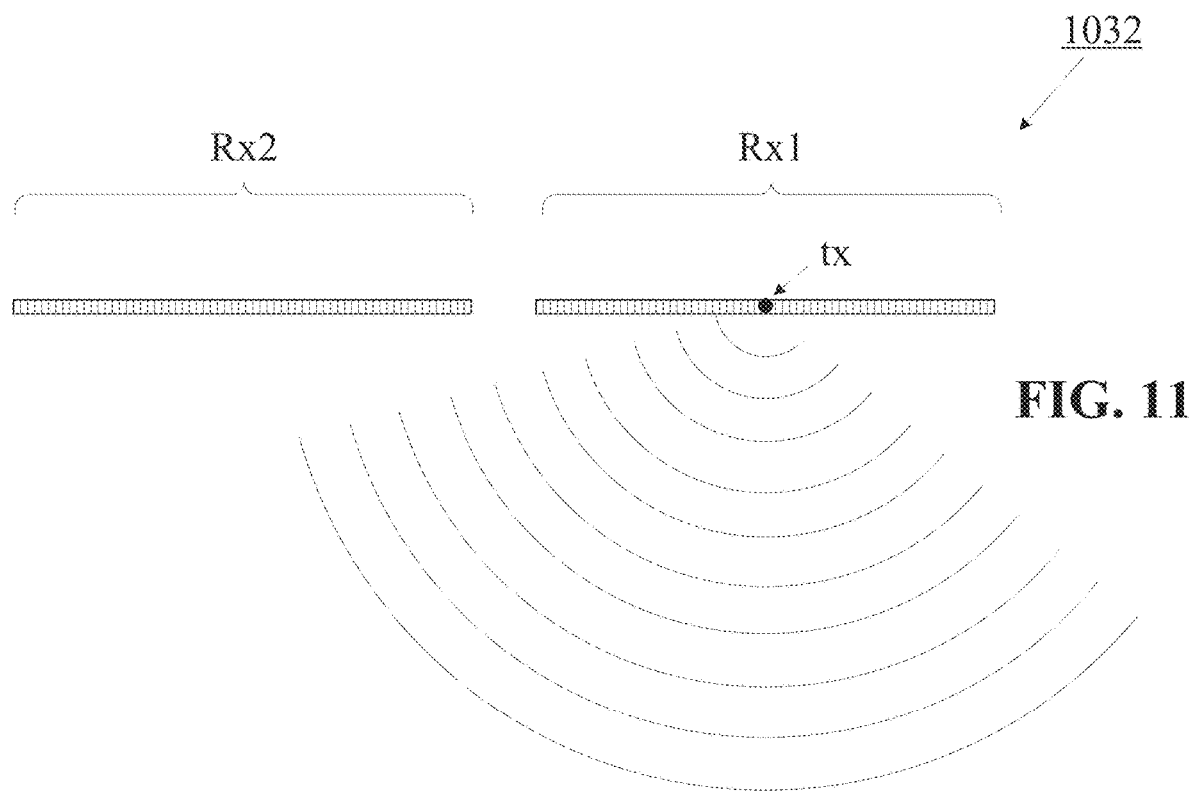
FIG. 11 is a schematic illustration of an ultrasound probe with two transducer arrays comprising many receive elements divided into two separate apertures. The right hand aperture is shown as having at least one transmit element.

In alternative embodiments, the same benefits may be achieved by utilizing multiple transmit apertures and a single receive aperture. For example, FIG. 10 illustrates a linear transducer array 1034 with transmit transducer elements on either end. In some embodiments, the array 1034 of FIG. 10 may be wide enough to include multiple receive apertures. Embodiments of each of these approaches are described in more detail below.

In some embodiments, a multiple aperture ultrasound probe with a total aperture that is two, three or more times greater than a maximum coherent aperture width for designed imaging scenarios may be used to increase the angle subtended by a point-source transmit aperture 'tx', a pixel to be evaluated, and each receive aperture. By increasing the angle between paths to a pixel being evaluated, the difference between measurements at different receive apertures will generally be larger and the inferred total flow and direction will be less prone to error. In some embodiments, a multiple aperture probe may be a two-aperture system such as the array 1032 shown in FIG. 11 or the array 1036 of FIG. 12. In other embodiments, a multiple aperture probe may be a three-aperture probe 1038 as shown in FIG. 13. Further embodiments provide many other possibilities such as placing one or more transmit apertures on an edge of a receive array instead of in the center, convex or concave curved arrays, or a plurality of transmit apertures positioned at varying points along an array. In some embodiments, more than one transmit aperture may be used and the Doppler results received by using each transmit aperture may be averaged with results from other transmit apertures to further improve results. An example of a probe 1034 with multiple transmit apertures is illustrated in FIG. 10.

Figure 14:
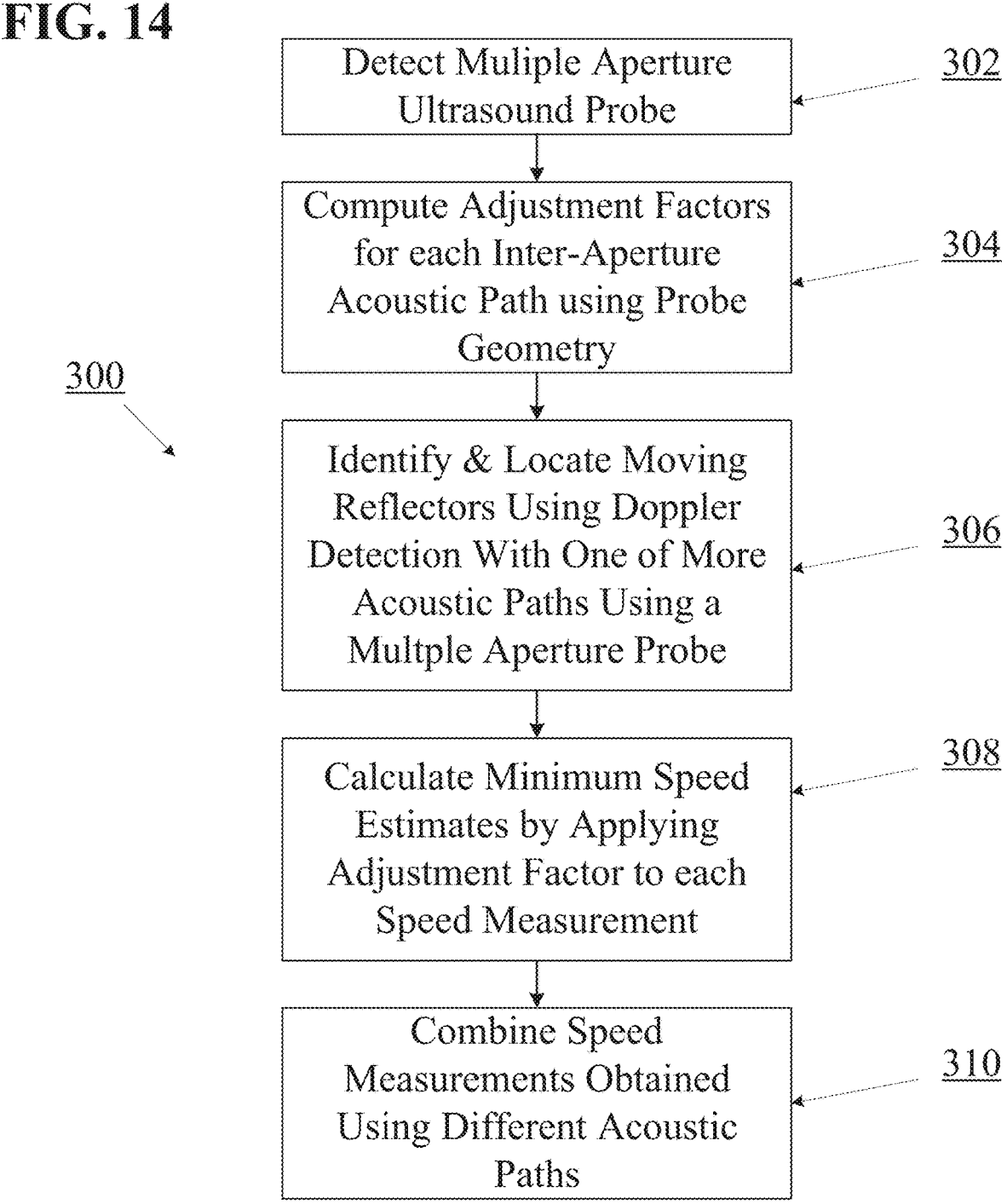
FIG. 14 is a flow chart illustrating an embodiment of a process for estimating the speed of a moving reflector using data independent approximation factors.

FIG. 14 illustrates an embodiment of a process 300 for detecting a scalar speed measurement using a multiple aperture ultrasound probe and making echo-data-independent approximations based on probe geometry. According to the process 300 of FIG. 14, the ultrasound imaging system may first determine 302 that a multiple aperture ultrasound probe is being used. Such identification 302 may occur by a handshake communication between a probe and an imaging system when a probe is connected. Alternatively, such detection 302 may simply involve determining that a stored data set was collected using a multiple aperture probe.

The process 300 may also involve computing or otherwise obtaining 304 an array of correction factors for each pixel in an image field (i.e., a correction factor for each acoustic path by which a particular reflector is to be imaged). As will be described in further detail below, a data independent approximation factor may be calculated for each inter-aperture acoustic path based on the geometry of transmit and receive apertures of the multiple aperture probe being used. Moving reflectors may be identified and located 306 using any available method, including those described herein. A minimum reflector speed may be calculated 308 by multiplying a measured speed by such a data independent approximation factor. Multiple speed measurements may be aggregated 310 by averaging, weighted averaging or any other method to further refine the accuracy of the minimum speed estimate.

Figure 15:
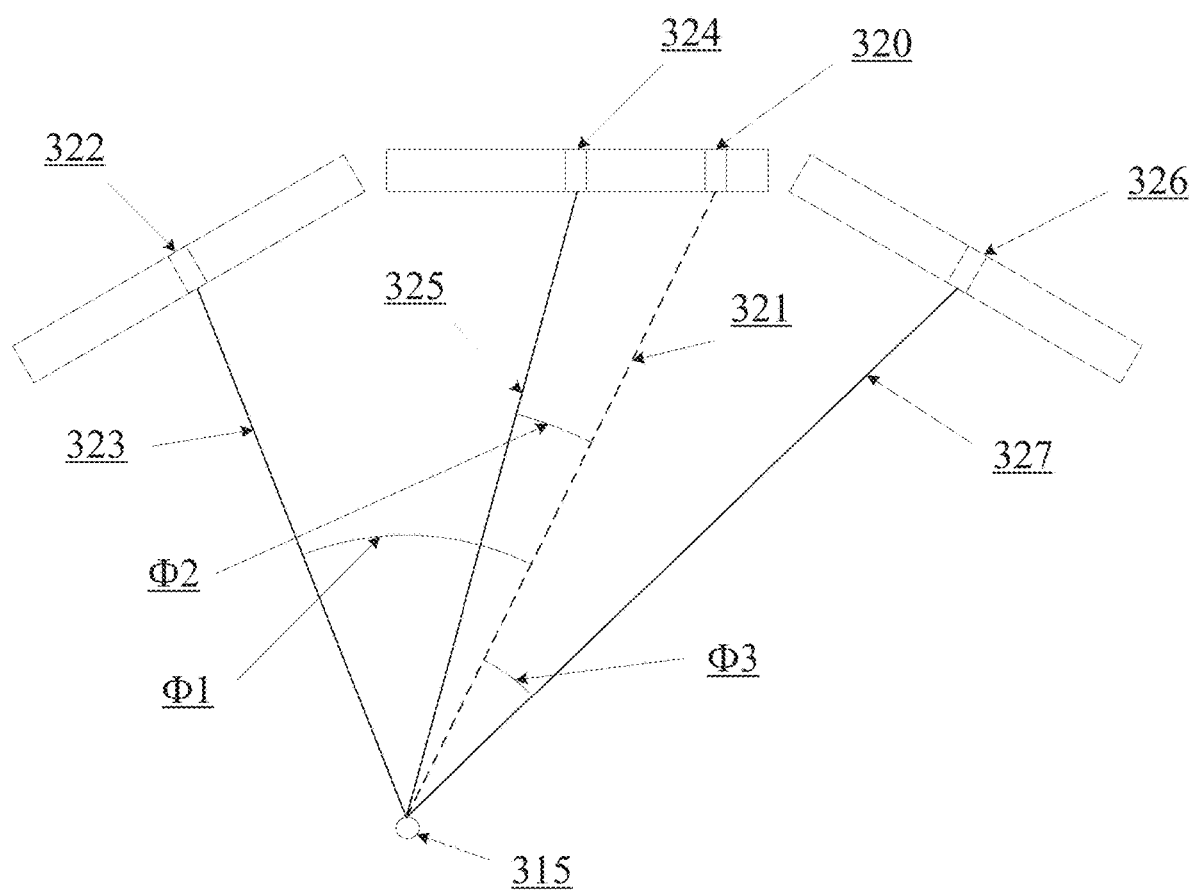
FIG. 15 is a schematic illustration of a multiple aperture imaging scenario.

With reference to FIG. 15 and as described in further detail below, the angle 11 between a first line 321 connecting a transmit aperture 320 and a pixel position 315 and second line connecting the pixel position 315 to a receive aperture 322 is dependent only on the known geometry of the probe and an image window being used. FIG. 15 further illustrates angles Φ2 and Φ3 between the transmit line 321 and the respective receive lines 325 and 327. As a result, the angle Φ may be pre-calculated for each combination of transmit aperture 320, pixel position 315 and receive aperture 322, 324 or 326 (i.e., for each acoustic path) for a given probe and image window. Once the angle Φ has been determined, a data independent approximation factor equal to 1/cos(Φ/2) may be pre-calculated for each pixel position and each acoustic window on that pixel. or any acoustic path for which Φ is zero (i.e., intra-aperture acoustic paths), the correction factor will simply be one (cos(0)=1). For any acoustic paths for which Φ is nearly zero, the correction factor may also be assumed to be one.

With reference again to FIG. 14, using any of the methods described above, or any other suitable method, Doppler frequency detection may be used to identify, locate and determine the speed of moving reflectors 306 at any (or every) pixel position using one or more acoustic paths. Then, for any given pixel, the speed acquired by each acoustic path may be multiplied 308 by the data independent approximation factor for that acoustic path to obtain a speed measurement representing the minimum speed of the reflector. Speed measurements obtained by multiple acoustic paths may be combined (such as by averaging or weighted averaging) to further improve accuracy of the measurement. In other embodiments, a maximum speed measurement obtained by multiple acoustic paths may be taken as the minimum speed measurement.

Figure 16:
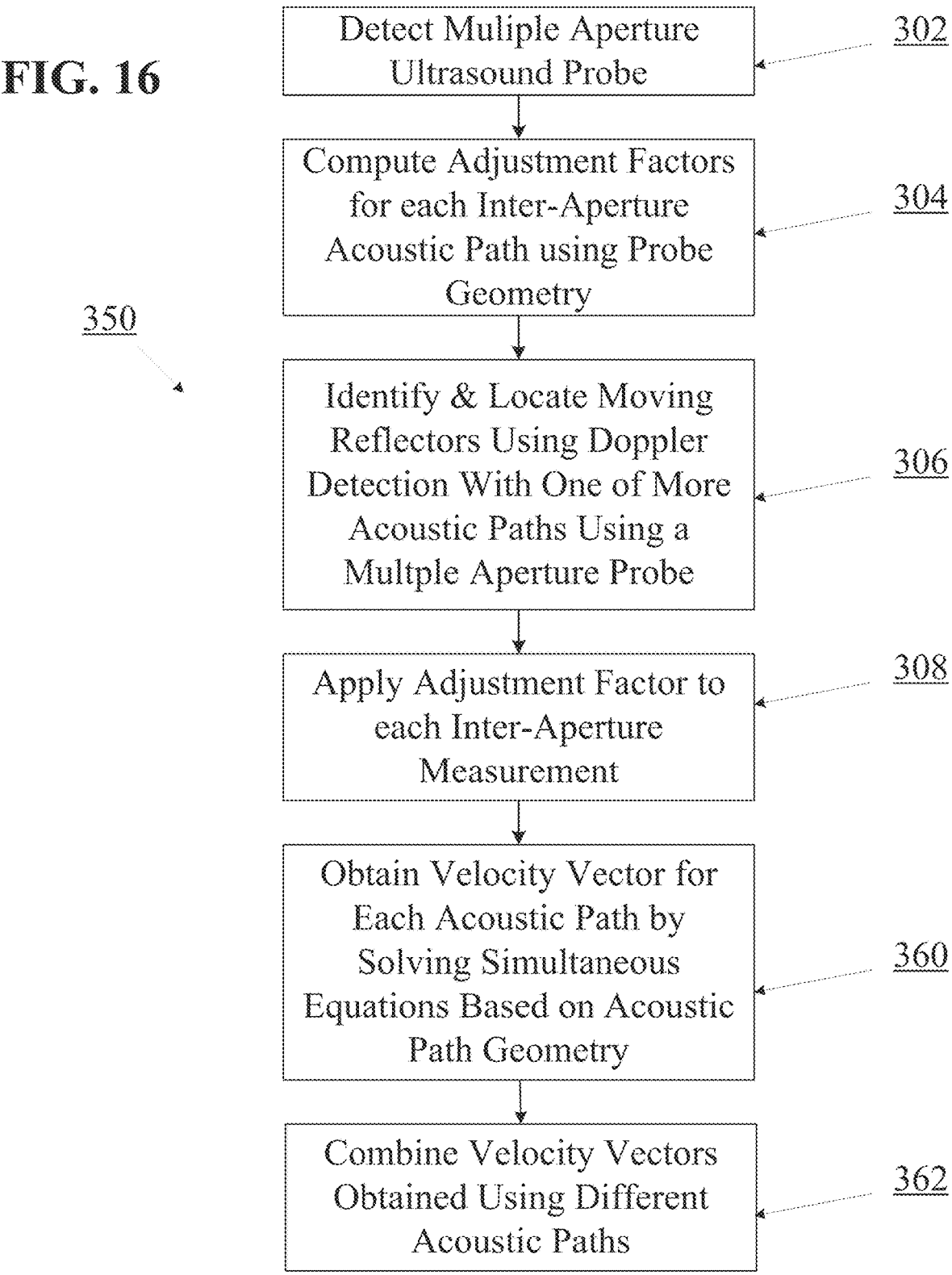
FIG. 16 is a flow chart illustrating an embodiment of a process for obtaining two-dimensional velocity vectors using a multiple aperture ultrasound imaging probe.

FIG. 16 illustrates an embodiment of a process 350 for detecting a two-dimensional velocity vector representing the speed and direction of a moving reflector within an image plane. The process 350 of FIG. 16 may begin with substantially the same steps as the process 300 of FIG. 14, including detecting the presence of a multiple aperture ultrasound probe 302, computing adjustment factors for the acoustic paths to be used 304, identifying and locating moving reflectors using a Doppler detection technique 306, and applying data independent adjustment factors 308. The data independent adjustment factors may be applied as corrections to the speed prior to calculating velocity direction. A velocity vector may then be calculated 360 by combining measurements obtained using two different acoustic paths. Speed and direction of motion of the reflector within the image plane may be calculated 360 by solving a set of simultaneous equations derived from the acoustic path geometry for the two paths used. An example of such simultaneous equations is provided below with reference to Equations 1-7.

Velocity vectors acquired using measurements from multiple pairs of acoustic paths may then be combined 362, such as by finding the cross product of the vectors. In some embodiments, one or more acoustic paths may be recognized (manually by a user or automatically by an imaging system or an image processing system) as more likely to provide an accurate measurement of the speed and direction of motion for a particular reflector. In such embodiments, velocity vectors obtained using such higher-quality acoustic paths may be given a higher weight when combining vectors obtained by multiple acoustic paths.

For simplicity of description, operation of a multiple aperture Doppler imaging system will be described with reference to the probe 1036 of FIG. 12. The extension of this analysis to the probe 1038 of FIG. 13 or any other possible probe configurations will be clear to the skilled artisan in view of the descriptions and illustrations herein.

Figure 12:
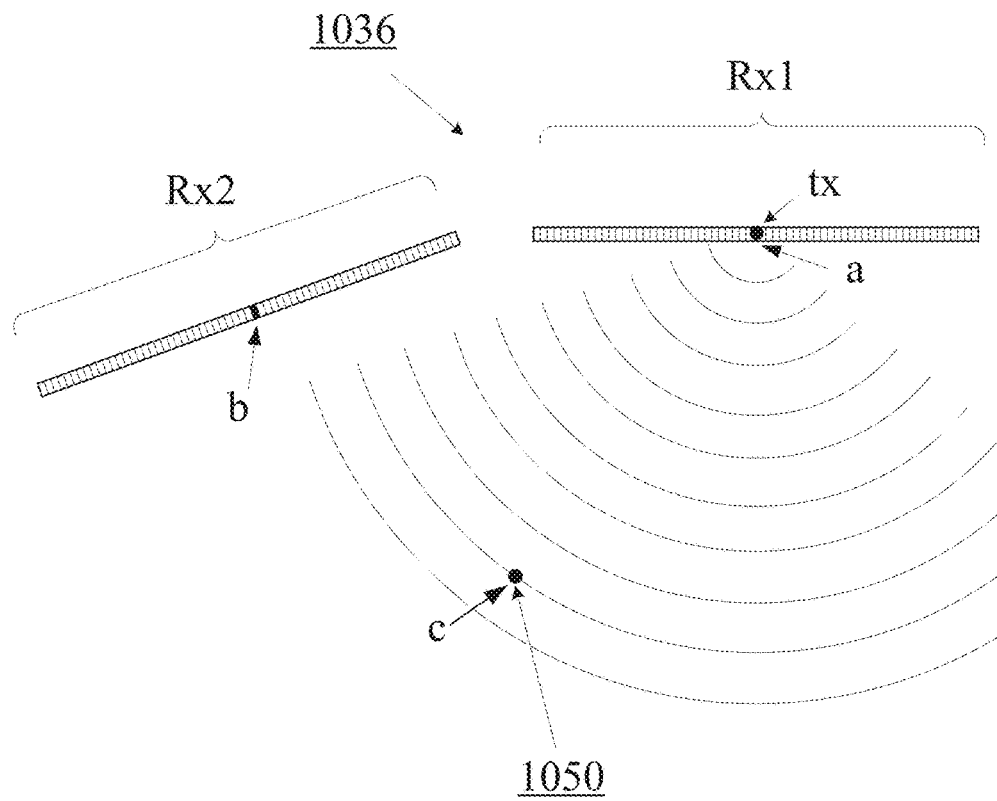
FIG. 12 is a multiple aperture probe comprising a horizontal transducer array with at least one designated transmit element and a second array of elements positioned at an angle relative to the first array.
Figure 13:
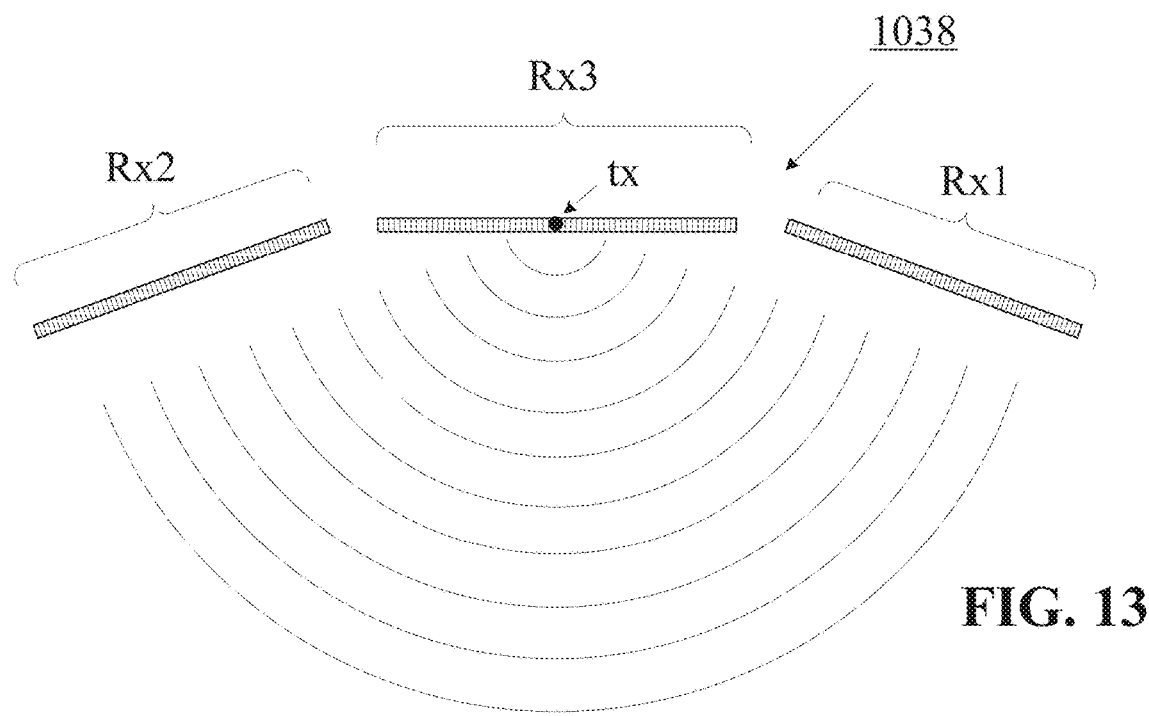
FIG. 13 is a multiple aperture probe comprising a horizontal array with at least one designated transmit element. A second and third array of elements are positioned on either side of the horizontal array and are shown oriented at an angle relative to the first array.

The probe 1036 of FIG. 12 comprises a first horizontal array with at least one designated transmit element 'tx' thereon. As shown, a transmit element may be located at a center of the first horizontal array. In some embodiments, transducer elements not used for transmit functions may be reserved for receive functions. The second array positioned either in line with or at an angle relative to the first array may be entirely designated for receiving echoes. The acoustic position of each element on each of the first and second arrays is preferably known precisely to at least a desired degree of accuracy.

Figure 17:
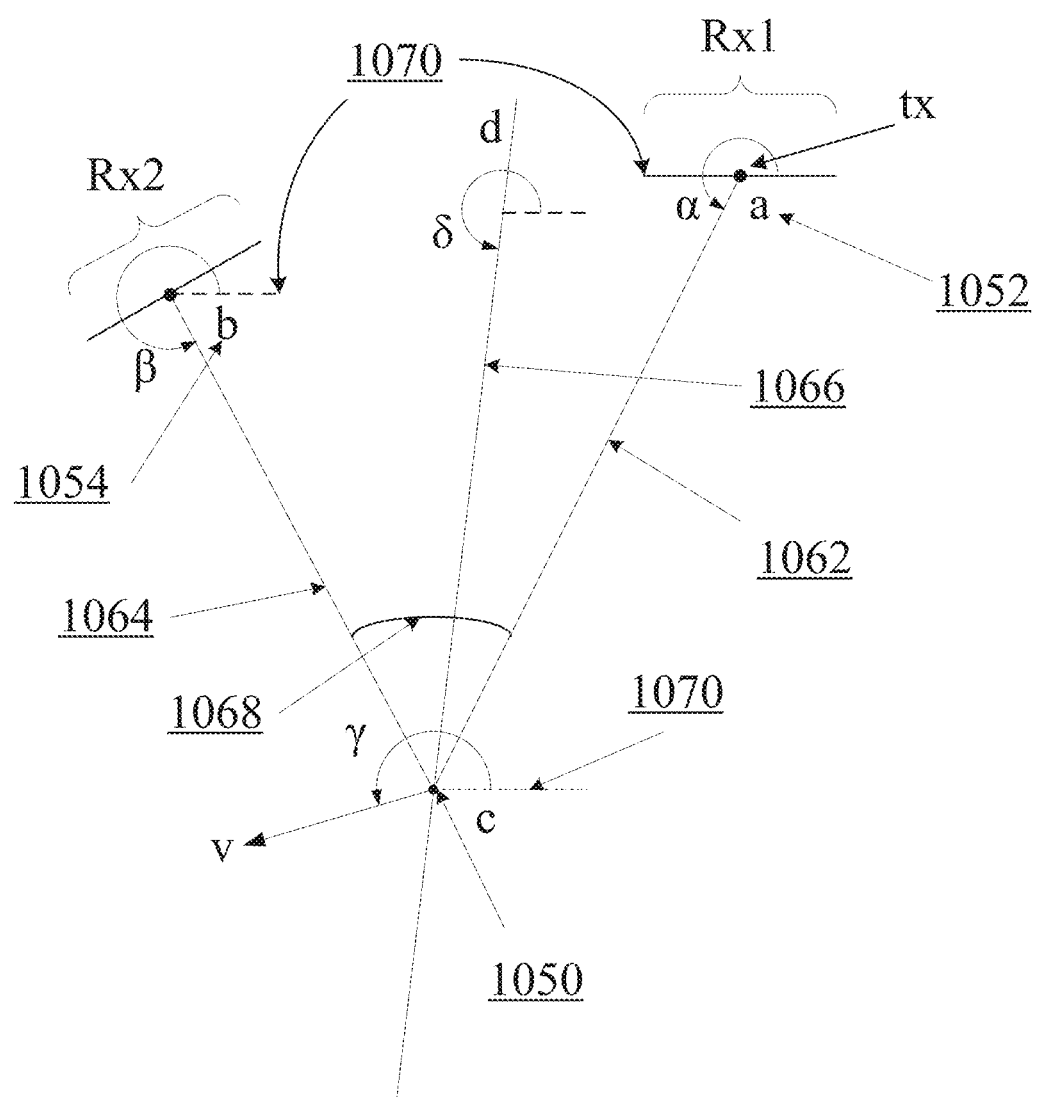
FIG. 17 is a schematic illustration showing aspects of one embodiment of a Doppler velocity measurement process using the system of FIG. 12.

FIG. 17 illustrates a further simplified representation of the system of FIG. 12. In FIG. 17, point c 1050 represents a test segment for which the velocity and direction of flow is to be estimated (referred to herein as the candidate point 1050). For the purpose of this discussion, the true velocity at point c 1050 is represented as V and the true direction is represented by angle γ. Point 'a' 1052 represents a center of the horizontal array and also corresponds to the location of the transmit aperture 'tx' as well as to the center of the first receive aperture 'Rx1'. Point 'b' represents the center element of the second receive aperture 'Rx2.'

Line 'a-c' 1062 represents the path of a transmitted wavefront traveling from the transmit element 'tx' to the candidate point 1050. Line 'a-c' 1062 also represents the path of an echo returning from the candidate point 1050 to the center of the first receive aperture 'Rx1'. Line 'b-c' 1064 represents the path of an echo traveling from the candidate point 1050 to the point 'b' 1054 on the second receive array 'Rx2'. Angle α is the angle of line 'a-c' 1062 relative to a horizontal reference line 1070. Similarly, angle β represents the angle of line 'b-c' 1064 relative to the same horizontal reference line 1070.

If candidate point 'c' 1050 is imaged by the first receive aperture 'Rx1' from echoes of pulses transmitted from the transmit aperture 'tx' (i.e., along acoustic path 'a-c'), Doppler information will be most sensitive to the component of motion along the line 'a-c' 1062. Imaging the same candidate point 'c' 1050 from the second receive aperture 'Rx2' with Doppler signals transmit from the transmit aperture 'tx' (i.e., along acoustic path 'a-c-b'), the most sensitive axis for Doppler information is the illustrated line 'd-c' 1066 which bisects the angle 'a-c-b' 1068. This is because the Doppler information (i.e. the increase or decrease in the frequency of received echoes relative to the transmitted Doppler ping frequency) will be affected by both the transmit and receive paths along line 'd-c' 1066. The angle of line 'd-c' 1066 from the horizontal reference 1070 is δ=(α+β)/2. As a result, without conducting any further analysis, the above-described one-dimensional methods of determining motion direction may be employed to measure the speed component along line 'd-c' 1066 of the reflector at point 'c'.

Figure 18:
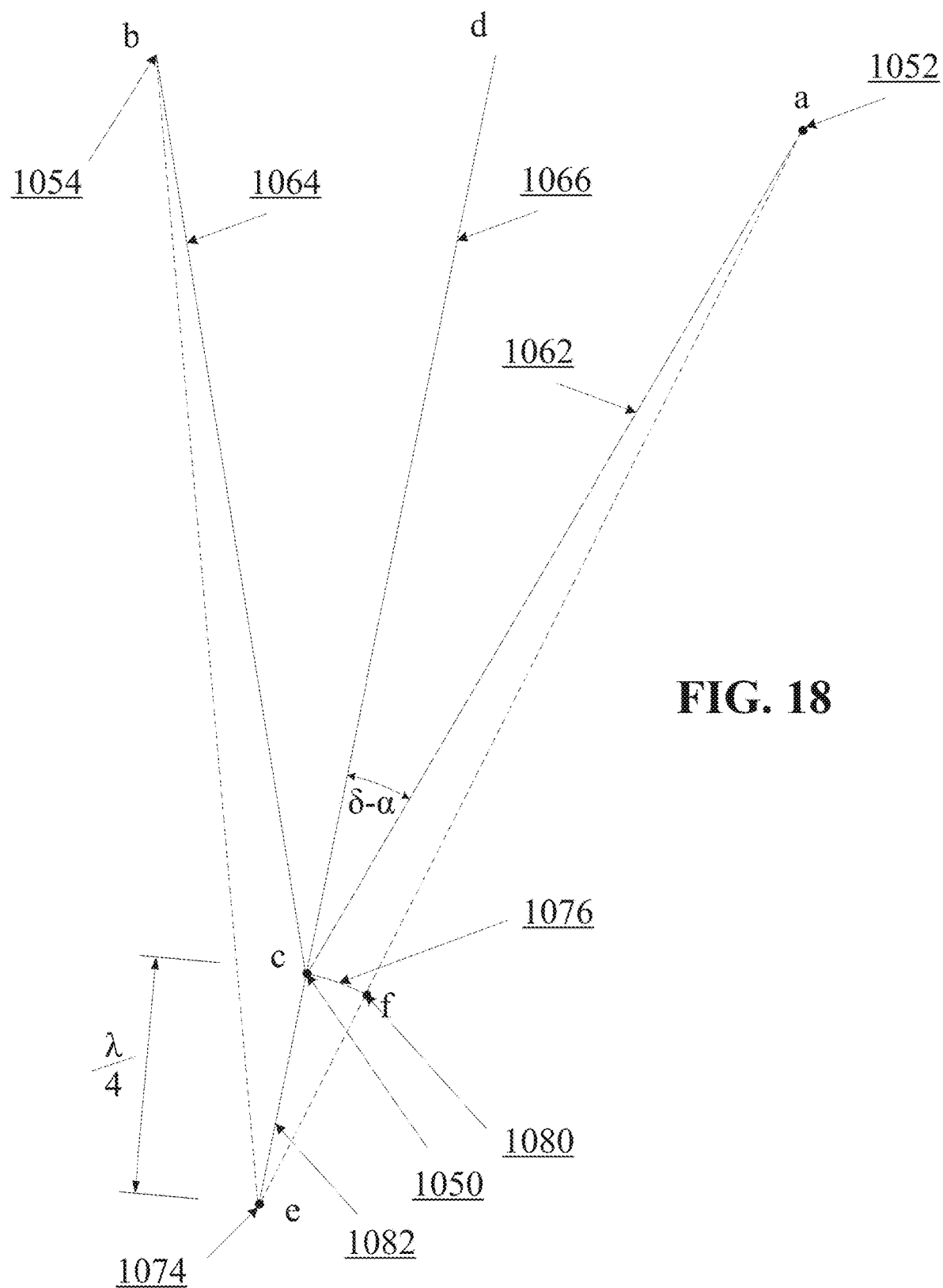
FIG. 18 is a schematic illustration showing aspects of an embodiment a Doppler velocity measurement process.

For this discussion, Vmax represents the maximum velocity detectable for a given Doppler ping frequency. As is well known in the art, the maximum Doppler frequency detectable without aliasing is PRF/2. In the context of ping-based Doppler, this means that the maximum Doppler frequency detectable without aliasing is half the transmitted Doppler ping frequency. The phase shift returned along the path 'a-c' by a particle at candidate point 'c' moving at Vmax is π radians per pulse. This is equivalent to a particle moving one quarter wavelength (λ/4) in the time between pulses. However, the same velocity along the path 'd-c' and sensed by phase shift along the path 'a-c-b' by the second receive aperture 'Rx2' results in a phase shift of only π cos(δ−α). This can be seen by reference to FIG. 18 where a particle at the candidate point 1050 is indicated as traveling along the path 'd-c' by a distance λ/4 to point e 1074 (distance is exaggerated in the figure). Dropping a perpendicular line 1076 to point 'f' 1080 on the line 'a-e' at point 'c' creates the triangle 'c-e-f' where the segment 'e-f' 1082 represents the increase in path length for the path 'a-c' as a reflector at point 'c' 1050 moves to the position of point 'e' 1074. Noting that the angle 'd-e-a' is almost equal to the angle 'd-c-a' (because the distance 'c-e' is very small), then 'e-f'∼=λ/4 cos(δ−α). Since this incremental path length is the same for the path 'c-b', the total phase shift is π cos(δ−α). Therefore all measurements along the path 'a-c-d' may be corrected by multiplying such measurements by 1/cos(δ−α).

Fortunately the angular difference and correction as calculated above, can be known in advance for each image pixel and is not dependent on transmit or echo data. This is because each image pixel maps to a known location within the region of interest, and because the acoustic position of each transducer element is known by the imaging system (e.g., as determined by a calibration system such as those discussed in Applicant's prior applications referenced above). Thus, for a chosen image depth, the angles δ and α for each image pixel and each transmit aperture/receive aperture combination (i.e., each acoustic path) can be calculated from the known probe geometry. Therefore an array of correction factors for each pixel at any chosen imaging depth or image window can be computed in advance and stored in memory for use during a Doppler measurement process. In other embodiments, such correction factors may be calculated dynamically.

Similar correction factors may be calculated for any inter-aperture acoustic path by determining the angle Φ formed by the transmit aperture, the reflector point and the receive element (e.g., as shown in FIG. 15), and then calculating the data independent correction factor as 1/cos (Φ/2) for that acoustic path. The correction factor for any intra-aperture acoustic path (for which Φ is zero) will be equal to one (since cos(0)=1).

$$\text{Correction for Doppler shift along path } a\text{-}c\text{-}b = 1/\cos(\delta - \alpha) \quad (1)$$

Assuming that this correction is made (and with respect to both transmit-receive paths for multiple aperture configurations such as that of FIG. 13), the computation for V and γ may proceed as follows.

Let $V_a$ be the measurement of V at point 'c' using the acoustic path 'd-c' and let $V_b$ be the measurement of V at point 'c' using the acoustic path 'a-c'. Then $$V_a = V \cos(\gamma - \alpha) \quad (2)$$

$$V_b = V \cos(\gamma - \delta) \quad (3)$$

Since $V_a$, $V_b$, α and δ are known or measured, V and γ can be found as follows:

$$\text{Let } K = V_a/V_b \quad (4)$$

If $V_b$ is not zero or near zero, $$\cos(\gamma - \alpha) = K \cos(\gamma - \delta)$$

$$\cos\gamma\cos\alpha + \sin\gamma\sin\alpha = K\cos\gamma\cos\delta + K\sin\gamma\sin\delta$$

$$(\cos\alpha - K\cos\delta)\cos\gamma = (K\sin\delta - \sin\alpha)\sin\gamma$$

$$\tan\gamma = (\cos\alpha - K\cos\delta)/(K\sin\delta - \sin\alpha) \text{ if } V_b \neq 0$$

$$\gamma = \arctan((\cos\alpha - K\cos\delta)/(K\sin\delta - \sin\alpha)) \text{ if } V_b \neq 0 \quad (5)$$

Alternatively, if $V_a$ is not zero or near zero, $$K'=V_b/V_a \quad (6)$$

$$\cos\gamma\cos\delta+\sin\gamma\sin\delta=K'(\cos\gamma\cos\alpha+\sin\gamma\sin\alpha)$$

$$(\cos\delta-K'\cos\alpha)\cos\gamma=(K'\sin\alpha-\sin\delta)\sin\gamma$$

$$\tan\gamma=(\cos\delta-K'\cos\alpha)/(K'\sin\alpha-\sin\delta) \text{ if } V_a\neq 0$$

$$\gamma=\arctan((\cos\delta-K'\cos\alpha)/(K'\sin\alpha-\sin\delta)) \text{ if } V_a\neq 0 \quad (7)$$

After using the appropriate equation to find γ, either of the equations (2) or (3) may be used to evaluate velocity V regardless of the direction of fluid flow.

For many applications the relatively complex computations of the equations (4) and (5) or (6) and (7) may not be justified. If one merely makes the corrections of equation (1), which are not data dependent (i.e., these values may be known based on probe geometry and imaging depth and pixel position without the need for any echo data), the maximum error in estimating total speed by using the equation:

$$S(\text{Speed})=(V_a+V_b)/2 \quad (8)$$

can be computed as follows:

$$S=V/2(\cos(\gamma-\alpha)+\cos(\gamma-\delta))$$

Maximum speed occurs when $$dS/d\gamma=-V/2(\sin(\gamma-\alpha)+\sin(\gamma-\delta))=0$$

Then $$\sin(\gamma-\alpha)=-\sin(\gamma-\delta)=\sin(\delta-\gamma)$$

$$\gamma-\alpha=\delta-\gamma$$

$$2\gamma=\alpha+\delta$$

$$\gamma=(\alpha+\delta)/2$$

Thus the maximum speed occurs when V is aligned with the angle $(\alpha+\delta)/2$.

The system is least sensitive to flow in the direction orthogonal to the line 'd-c', namely, $(\alpha+\delta)/2+\pi/2$.

$$S = V/2[\cos((-\alpha+\delta+\pi)/2) + \cos((\alpha-\delta+\pi)/2)]$$
$$= V/2[\sin((\delta-\alpha)/2) + \sin((\delta-\alpha)/2)]$$
$$= V\sin((\delta-\alpha)/2)$$

In any region of the image where the angle $(\delta-\alpha)$ is greater than 30 degrees, velocities in the orthogonal direction will be underreported by no more than 50% using this simplification.

For flow aligned with the angle $(\alpha+\delta)/2$, $$S=V\cos((\delta-\alpha)/2).$$

Therefore in any region for which $(\delta-\alpha)/2$ is less than 60 degrees, velocity components in the direction $(\alpha+\delta)/2$ will also be underreported by no more than 50% using this simplification.

In contrast, velocities estimated by single-angle (or one-dimensional) color flow Doppler can completely miss velocities in the direction orthogonal to the angle of measurement.

In the above analysis, calculations are performed using the center of the receive aperture rx based on the assumptions that the receive apertures are symmetrical about the center point, and echoes received by the individual elements of the receive aperture are summed coherently prior to performing the velocity calculations. In other embodiments, any other point on the receive aperture may be used in the above velocity calculations. In further embodiments, the above may be extended to separately calculate velocities as measured by each individual element of the receive aperture.

Similarly, the above analysis may also be extended to systems utilizing more than two receive apertures, and/or more than one transmit aperture as will be clear to the skilled artisan in view of the descriptions herein. For example, the above analysis may be applied to an ultrasound probe including a third receive aperture, such as the center array 'rx3' in FIG. 13. In such embodiments, a first measure of the velocity of any given moving reflector 'c' may be calculated using the above analysis as applied to the center receive aperture 'rx3' and the left receive aperture 'rx2'. A second measure of the velocity of the reflector 'c' may be calculated using the above analysis as applied to the center receive aperture 'rx3' and the right receive aperture 'rx1'. The first and second velocity vectors may then be averaged to obtain a final velocity measurement. In some embodiments, the first and second velocity vectors may be combined with a weighted average that gives more weight to the transmit/receive aperture pair that provides the best view of the point being measured. Similarly, velocity vectors measured using two transmit apertures and one or more receive apertures may be averaged to improve accuracy of a velocity measurement.

For example, in some embodiments, the above process may be used to obtain velocity measurements using a second, third, fourth, fifth (or any number of additional) receive apertures simultaneously with a first receive aperture. In such embodiments, velocity magnitude and direction measurements obtained from all receive apertures may be combined (e.g., by averaging or weighted averaging) to further increase the accuracy of such measurements.

Non-Doppler Motion Detection

Figure 20:
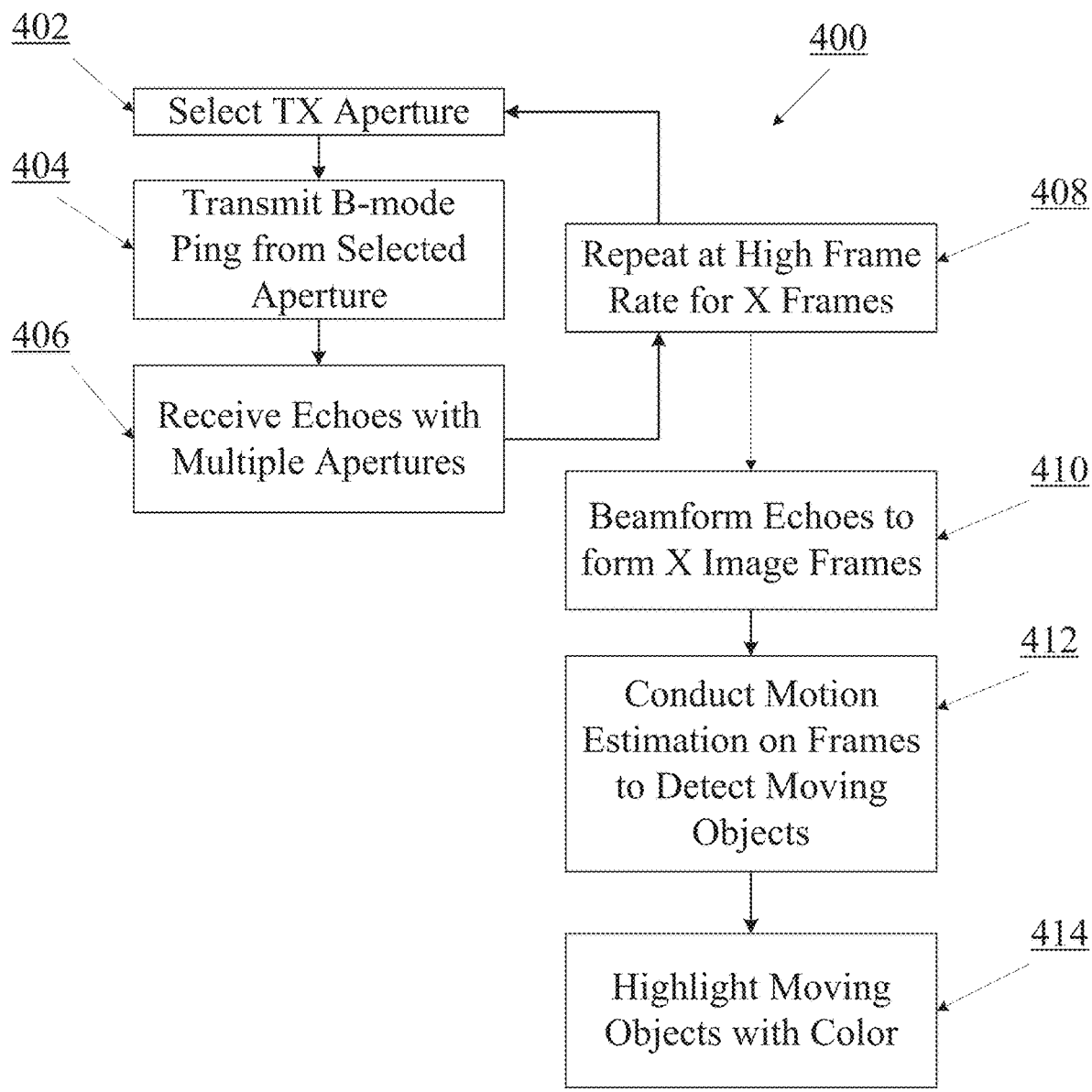
FIG. 20 is a flow chart illustrating an embodiment of a process for detecting motion using a ping-based imaging system without detecting Doppler shifts.

FIG. 20 illustrates an example of a process 400 by which motion may be detected using a ping-based imaging system without the need to detect Doppler frequencies. Such embodiments may use high-frame-rate ping imaging and image processing techniques to detect motion of imaged pixels. Because a complete image may be computed from echoes of a single transmit ping (as described above and in Applicant's prior applications referenced above), ping images may be obtained at a frame rate as high as a maximum possible ping repetition rate, which is limited only by the round-trip travel time of a single ping signal. In other words, because only a single ping is needed to form an image, the only significant limit on frame rate is the speed of ultrasound sound in the imaged medium. For example, in some embodiments a ping-based imaging system can achieve a frame rate of 4000 frames per second or higher when imaging to a depth of 18 cm with a sequence of images at a sufficiently high frame rate, motion of objects may be seen directly. Furthermore, computer analysis of a sequence of high-frame-rate images may be conducted in order to automatically identify and highlight motion using color flow or any other technique.

Thus, in some embodiments, a process 400 for non-Doppler motion detection method may comprise obtaining a single frame by selecting a transmit aperture 402, transmitting a B-mode ping 404, receiving echoes of the B-mode ping with multiple apertures 406. Steps 402-406 may be repeated 408 to obtain several frames (e.g., tens, hundreds or thousands of frames). (In some embodiments, steps 402-406 may be repeated with a different transmit aperture to obtain additional data for the first frame.) Each frame may then be beamformed to obtain a series of images 410.

In some embodiments, automated analysis of the sequence of high frame rate images may then be conducted 412 using any of the many known motion estimation techniques commonly used in image processing. Using such techniques, fast moving reflectors (such as blood or fluid in a pipe) may be distinguished from the slower motion of stationary or slowly moving objects (such as a pipe wall, a blood vessel wall or solid tissue). Changes in pixel values faster than those expected from stationary or slowly-moving objects may be detected as motion and displayed as color superimposed on a B-mode image. The pixels identified as representing moving objects or substances may then be highlighted 414, such as by applying color with an intensity or shade that varies depending on direction and speed of motion similar to other embodiments described herein. In some embodiments, signal processing such as frequency analysis on a per pixel basis over several frames may be used to distinguish between fast moving small reflectors and slow moving large reflectors. In various embodiments, such techniques may be used to determine motion velocity vectors in any direction within the imaged region of interest.

Displaying Motion Information

Whether motion is detected using Doppler techniques or high-frame-rate motion estimation techniques, one or more threshold values may be established to provide a test for distinguishing "fast moving" points from "slow moving" or "stationary" points. In various embodiments, threshold values may be established manually by a user or automatically by a software agent based on factors such as an analysis of detected motion and/or information about expected ranges of motion in a known imaged object. In some embodiments, slow moving or stationary points may be displayed with different colors or intensities than fast moving points.

With respect to color flow Doppler, embodiments of the present invention can potentially provide too much information for a usable display. In some embodiments, one may color code every angle of flow with a different color, but interpretation of such colors might be confusing. One important use of color flow Doppler in current medical practice is the detection of regurgitation and turbulence of blood flow. For these purposes a two color system may be desirable.

In such embodiments, in a local area where flow is detected, the maximum axis for flow (such as along an artery or through a valve) may be determined. Then movement in one direction along the maximum flow axis may be indicated by shades of one color (such as red, for example), and movement in the opposite direction may be indicated by another color (such as blue, for example). Thus, in some embodiments, all directions may be displayed as either red or blue based on finding the component of each direction along the maximum axis.

In such embodiments, the ultrasound imaging system or an image display workstation may be configured with a user interface with which a user may identify an axis (single dimension) or a coordinate system (two-dimensions) for which colors should be assigned. For example, a user may identify a single-dimension, such that each pixel in the image may be assigned a color (e.g., red or blue) depending on a sign and a magnitude of a velocity component along the selected axis. In other embodiments, a two-dimensional color system may be defined such that at least a third color may be applied based on a velocity component along a second axis. In various embodiments, one, two or more axes of predominant flow may be identified automatically by software analysis of motion data, or manually by a user through a suitable user interface. For example, an axis of predominant motion may be determined by calculating an average of all (or several) velocity vectors.

For example, a coordinate system may be defined such that pixels with positive components of velocity along a horizontal axis are colored red with an intensity proportional to the magnitude of the velocity component along the horizontal axis. In the same example, pixels with negative components of velocity along the horizontal axis may be colored blue with an intensity proportional to the magnitude of the negative horizontal velocity component. Pixels with positive components of velocity along a vertical axis may then be colored with another color, such as yellow, with an intensity proportional to the magnitude of the positive vertical velocity component. Any other coordinate system (e.g., radial coordinates or non-orthogonal coordinate systems) and color scheme may also be used.

For more complex situations in which fluid flow does not have a predominant direction, a display employing a different color for every angle of flow may be preferred.

Spectral Doppler is a form of ultrasound image display in which the spectrum of flow velocities is represented graphically on the Y-axis and time on the X-axis. In some embodiments, all of the data needed for spectral analysis may be available for every pixel in the B-mode image. Controls would be necessary to position a cursor to the area of interest and to determine the size of the sample to combine centered on the cursor position.

In some embodiments, similar techniques to those discussed above may be used for what has been called "Power Doppler" in the art. Power Doppler is non-directional and has been used to detect very low flow rates. To discriminate between very low flow rates, the system may need to transmit a longer Doppler ping to achieve more samples at the Doppler ping frequency. This may have the effect of reducing the frame rate. In some embodiments, the directional information may be discarded as is traditional in power Doppler, or directional information may be displayed as described above with respect to color Doppler.

Memory Architecture

Various embodiments of the systems and methods described above may be further enhanced by using an ultrasound imaging system configured to store digitized echo waveforms during an imaging session. Such digital echo data may be subsequently processed on an imaging system or on an independent computer or other workstation configured to beamform and process the echo data to form images. In some embodiments, such a workstation device may comprise any digital processing system with software for dynamically beamforming and processing echo data using any of the techniques described above.

Figure 19:
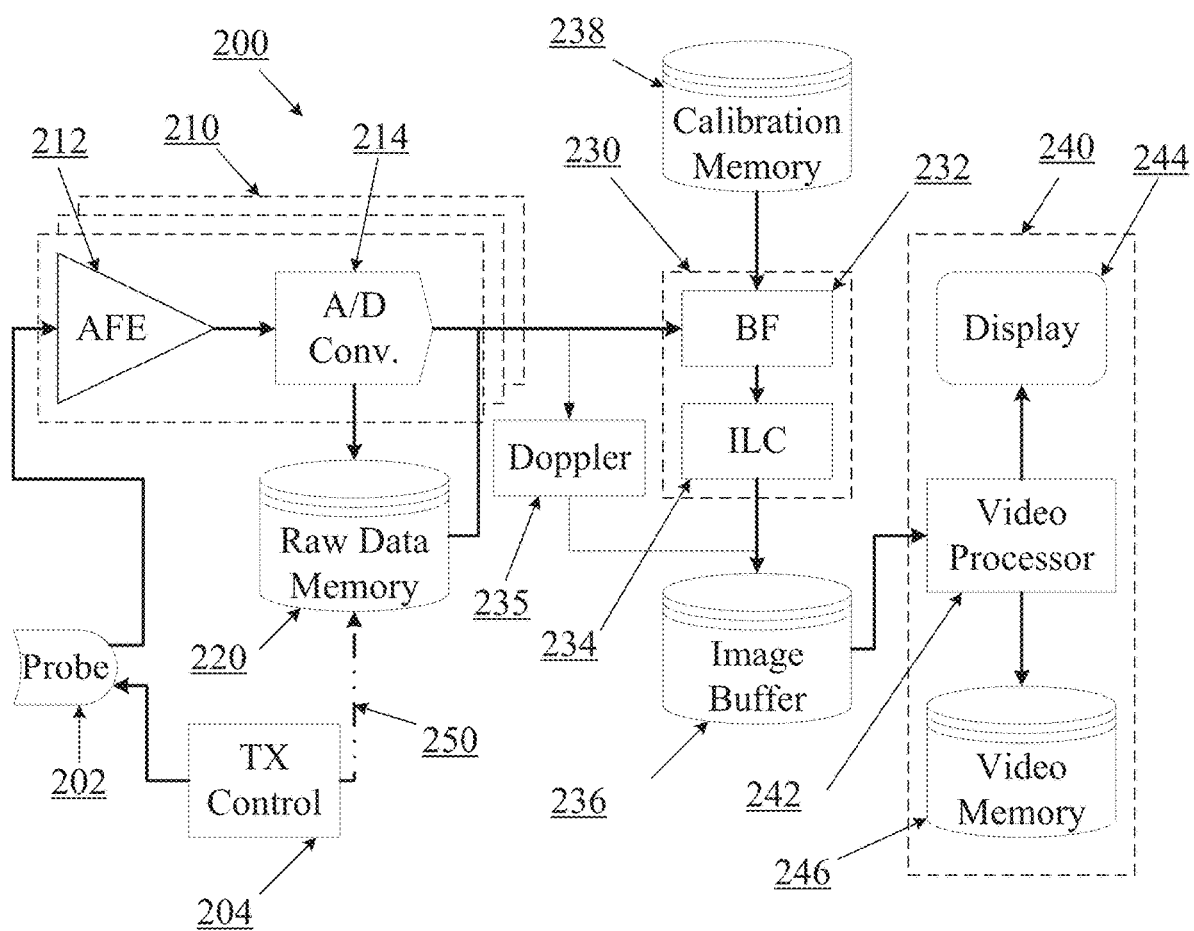
FIG. 19 is a block diagram illustrating components of an ultrasound imaging system.

FIG. 19 is a block diagram illustrating components that may be included in some embodiments of an ultrasound imaging system configured for storing echo data. The diagram of FIG. 19 includes several subsystems: a transmit control subsystem 204, a probe subsystem 202, a receive subsystem 210, an image generation subsystem 230, and a video subsystem 240. Unlike most ultrasound systems, the system of FIG. 19 provides a memory device configured to store raw un-beamformed echo data for later retrieval and processing.

In various embodiments, received echo data may be stored at various stages from pure analog echo signals to fully processed digital images or even digital video. For example, a purely raw analog signal may be stored using an analog recording medium such as analog magnetic tape. At a slightly higher level of processing, digital data may be stored immediately after passing the analog signal through an analog-to-digital converter. Further processing, such as band-pass filtering, interpolation, down-sampling, up-sampling, other filtering, etc. may be performed on the digitized echo data, and raw data may be stored after such additional filtering or processing steps. Such raw data may then be beamformed to determine a pixel location for each received echo, thereby forming an image. Individual images may be combined as frames to form video. In some embodiments, it may be desirable to store digitized echo data after performing very little processing (e.g., after some filtering and conditioning of digital echo data, but before performing any beamforming or image processing). Some ultrasound systems store beamformed echo data or fully processed image data. Nonetheless, as used herein, the phrases "raw echo data" and "raw data" may refer to stored echo information describing received ultrasound echoes (RX data) at any level of processing prior to beamforming. Raw echo data may include echo data resulting from B-mode pings, Doppler pings, or any other ultrasound transmit signal.

In addition to received echo data, it may also be desirable to store information about one or more ultrasound transmit signals that generated a particular set of echo data. For example, when imaging with a multiple aperture ping ultrasound method as described above, it is desirable to know information about a transmitted ping that produced a particular set of echoes. Such information may include the identity and/or position of one or more a transmit elements as well as a frequency, magnitude, pulse length, duration or other information describing a transmitted ultrasound signal. Transmit data is collectively referred herein to as "TX data". In some embodiments, such TX data may be stored explicitly in the same raw data memory device in which raw echo data is stored. For example, TX data describing a transmitted signal may be stored as a header before or as a footer after a set of raw echo data generated by the transmitted signal. In other embodiments, TX data may be stored explicitly in a separate memory device that is also accessible to a system performing a beamforming process. In embodiments in which transmit data is stored explicitly, the phrases "raw echo data" or "raw data" may also include such explicitly stored TX data. In still further embodiments, transducer element position information may be explicitly stored in the same or a separate memory device. Such element position data may be referred to as "calibration data" or "element position data", and in some embodiments may be generally included within "raw data."

TX data may also be stored implicitly. For example, if an imaging system is configured to transmit consistently defined ultrasound signals (e.g., consistent magnitude, shape, frequency, duration, etc.) in a consistent or known sequence, then such information may be assumed during a beamforming process. In such cases, the only information that needs to be associated with the echo data is the position (or identity) of the transmit transducer(s). In some embodiments, such information may be implicitly obtained based on the organization of raw echo data in a raw data memory. For example, a system may be configured to store a fixed number of echo records following each ping. In such embodiments, echoes from a first ping may be stored at memory positions 0 through 'n' (where 'n' is the number of records stored for each ping), and echoes from a second ping may be stored at memory positions n+1 through 2n+1. In other embodiments, one or more empty records may be left in between echo sets. In some embodiments received echo data may be stored using various memory interleaving techniques to imply a relationship between a transmitted ping and a received echo data point (or a group of echoes). Similarly, assuming data is sampled at a consistent, known sampling rate, the time at which each echo data point was received may be inferred from the position of that data point in memory. In some embodiments, the same techniques may also be used to implicitly store data from multiple receive channels in a single raw data memory device.

As shown in FIG. 19, an ultrasound imaging system 200 may comprise an ultrasound probe 202 which may include a plurality of individual ultrasound transducer elements, some of which may be designated as transmit elements, and others of which may be designated as receive elements. In some embodiments, each probe transducer element may convert ultrasound vibrations into time-varying electrical signals and vice versa. In some embodiments, the probe 202 may include any number of ultrasound transducer arrays in any desired configuration. A probe 202 used in connection with the systems and methods described herein may be of any configuration as desired, including single aperture and multiple aperture probes.

The transmission of ultrasound signals from elements of the probe 202 may be controlled by a transmit controller 204. Upon receiving echoes of transmit signals, the probe elements may generate time-varying electric signals corresponding to the received ultrasound vibrations. Signals representing the received echoes may be output from the probe 202 and sent to a receive subsystem 210. In some embodiments, the receive subsystem may include multiple channels, each of which may include an analog front-end device ("AFE") 212 and an analog-to-digital conversion device (ADC) 214. In some embodiments, each channel of the receive subsystem 210 may also include digital filters and data conditioners (not shown) after the ADC 214. In some embodiments, analog filters prior to the ADC 214 may also be provided. The output of each ADC 214 may be directed into a raw data memory device 220. In some embodiments, an independent channel of the receive subsystem 210 may be provided for each receive transducer element of the probe 202. In other embodiments, two or more transducer elements may share a common receive channel.

In some embodiments, an analog front-end device 212 (AFE) may perform certain filtering processes before passing the signal to an analog-to-digital conversion device 214 (ADC). The ADC 214 may be configured to convert received analog signals into a series of digital data points at some predetermined sampling rate. Unlike most ultrasound systems, some embodiments of the ultrasound imaging system of FIG. 19 may then store digital data representing the timing, phase, magnitude and/or the frequency of ultrasound echo signals received by each individual receive element in a raw data memory device 220 before performing any further beamforming, filtering, image layer combining or other image processing.

In order to convert the captured digital samples into an image, the data into an image, the data may be retrieved from the raw data memory 220 by an image generation subsystem 230. As shown, the image generation subsystem 230 may include a beamforming block 232 and an image layer combining ("ILC") block 234. In some embodiments, a beamformer 232 may be in communication with a calibration memory 238 that contains probe calibration data. Probe calibration data may include information about the precise acoustic position, operational quality, and/or other information about individual probe transducer elements. The calibration memory 238 may be physically located within the probe, within the imaging system, or in location external to both the probe and the imaging system.

In some embodiments, after passing through the image generation block 230, image data may then be stored in an image buffer memory 236 which may store beamformed and (in some embodiments) layer-combined image frames. A video processor 242 within a video subsystem 240 may then retrieve image frames from the image buffer, and may process the images into a video stream that may be displayed on a video display 244 and/or stored in a video memory 246 as a digital video clip, e.g. as referred to in the art as a "cine loop".

In some embodiments, the transmit controller 204 may include any combination of analog and digital components for controlling transducer elements of the probe 202 to transmit un-focused ultrasound pings at desired frequencies and intervals from selected transmit apertures according to a desired imaging algorithm. In some embodiments a transmit controller 204 may be configured to transmit ultrasound pings at a range of ultrasound frequencies. In some (though not all) embodiments, the transmit controller may also be configured to operate as a phased array, transmitting focused (i.e. transmit beamformed) ultrasound scanline beams.

In some embodiments, the AFE 212 may be configured to perform various amplification and filtering processes to a received analog signal before passing the analog signal to an analog-to-digital conversion device. For example, an AFE 212 may include amplifiers such as a low noise amplifier (LNA), a variable gain amplifier (VGA), a bandpass filter, and/or other amplification or filtering devices. In some embodiments, an AFE device 212 may be configured to begin passing an analog signal to an ADC 214 upon receiving a trigger signal. In other embodiments, an AFE device can be "free running", continuously passing an analog signal to an ADC.

In some embodiments, each analog-to-digital converter 214 may generally include any device configured to sample a received analog signal at some consistent, predetermined sampling rate. For example, in some embodiments, an analog-to-digital converter may be configured to record digital samples of a time-varying analog signal at 25 MHz, which is 25 million samples per second or one sample every 40 nanoseconds. Thus, data sampled by an ADC may simply include a list of data points, each of which may correspond to a signal value at a particular instant. In some embodiments, an ADC 214 may be configured to begin digitally sampling an analog signal upon receiving a trigger signal. In other embodiments, an ADC device can be "free running", continuously sampling a received analog signal.

In some embodiments, the raw data memory device 220 may include any suitable volatile or non-volatile digital memory storage device. In some embodiments, the raw data memory 220 may also comprise communication electronics for transmitting raw digital ultrasound data to an external device over a wired or wireless network. In such cases, the transmitted raw echo data may be stored on the external device in any desired format. In other embodiments, the raw data memory 220 may include a combination of volatile memory, non-volatile memory and communication electronics.

In some embodiments, the raw data memory device 220 may comprise a temporary (volatile or non-volatile) memory section, and a long-term non-volatile memory section. In an example of such embodiments, the temporary memory may act as a buffer between the ADC and the beamformer in cases where the beamformer may be unable to operate fast enough to accommodate data at the full rate from the ADC.

In some embodiments, a long-term non-volatile memory device may be configured to receive data from a temporary memory device or directly from the ADC. Such a long-term memory device may be configured to store a quantity of raw echo data for subsequent processing, analysis or transmission to an external device.

In some embodiments, the quantity of data in the raw data memory may depend on the digital sampling rate, the size of each data sample (in bits or bytes), any data compression applied and other factors. Thus, in some embodiments, a memory device with a capacity of about 2 GB may store raw echo data corresponding to about six seconds of real-time display. In other embodiments, data representing a shorter or longer period of time may be stored in the same amount of memory.

In some embodiments, the beamforming block 232 and the image layer combining block 234 may each include any digital signal processing and/or computing components configured to perform the specified processes (e.g., as described below). For example, in various embodiments the beamforming 232 and image layer combining 234 may be performed by software running on a GPU or by firmware running on an FPGA architecture.

In some embodiments, the video processor 242 may include any video processing hardware, firmware and software components that may be configured to assemble image frames into a video stream for display and/or storage.

In some embodiments, echo data may be received, beamformed, processed and displayed in substantially real-time (with some latency in some embodiments), while simultaneously storing echo data in a memory device. In some such embodiments, processing and/or beamforming for real-time display may include retrieving echo data resulting from multiple pings from a memory device (which may operate in a circular buffer mode), and beamforming or processing may be performed simultaneously on echo data received from a plurality of pings transmitted at different times. In other embodiments, echo data may be stored in a long term memory storage device, and may be beamformed and processed for display at a much later time, and/or using entirely different computing hardware than the system used to transmit and receive ultrasound signals. Such a separate computing system may generally be referred to as an imaging workstation.

During an imaging session in which Doppler ping signals are transmitted as described as in one or more of the above embodiments, substantially un-processed echo data may be captured and stored using the apparatus described above (or an equivalent apparatus). Such raw echo data may be captured and stored whether or not the echoes are processed to display the results of a Doppler analysis during the initial imaging session. Thus, in some embodiments, echoes received from Doppler pings may be interpreted or analyzed using only the captured raw echo data retrieved from a raw data memory device and any other available information about the imaging session (such as corresponding TX data describing the Doppler pings).

In one example, multiple aperture Doppler patterns may be transmitted during an imaging session, and the resulting Doppler echo data may be captured and stored without processing or displaying color flow Doppler during the live imaging session. The stored raw echo data may be later retrieved from memory and processed using the same or different processing hardware in order to visualize and analyze the results of the Doppler imaging. In another example, multiple aperture Doppler patterns may be transmitted during an imaging session in between or simultaneously with B-mode imaging signals, and both the resulting Doppler echo data and the resulting B-mode imaging data may be received, captured and stored while simultaneously beamforming, processing and displaying the B-mode image and the Doppler image on a single display (e.g., in an overlay image or as separate side-by-side images).

Generating ultrasound images using a multiple aperture ping imaging process means that images from an entire region of interest are "in focus" at all times. This is true because each transmitted ping illuminates the entire region, receive apertures receive echoes from the entire region, and the dynamic multiple aperture beamforming process may form an image of any part or all of the insonified region. In such cases, the maximum extent of the image may be primarily limited by attenuation and signal-to-noise factors rather than by the confined focus of a transmit or receive beamforming apparatus. As a result, a full-resolution image may be formed from any portion of a region of interest using the same set of raw echo data. As used herein, the term "image window" will be used to refer to a selected portion of an entire insonified region of interest. In some embodiments, simultaneous images may be formed of multiple overlapping or non-overlapping areas (image windows) within the insonified region.

In the same way, color flow images (or other images highlighting motion of one or more imaged region) may be formed from any selected area within an insonified region of interest. Thus, in some embodiments, echo data may be retrieved from a memory device, and image windows may be defined entirely independent of the imaging window used during a live imaging session. In such embodiments, Doppler echo data may be evaluated independently of choices made during a live imaging session. For example, when re-processing echo data retrieved from a memory device, factors such as an image window, an axis (or axes) of motion, "fast" vs. "slow" movement threshold values, a Doppler motion estimation algorithm, speed-of-sound assumptions, weighting factors, various filtering (e.g., de-convolution filtering or matched filtering), calibration data, TX data, transducer-element-to-aperture groupings, or any other piece of information used in B-mode or Doppler analysis, beamforming or image processing may be changed relative to the values used during a live imaging session.

Figure 21:
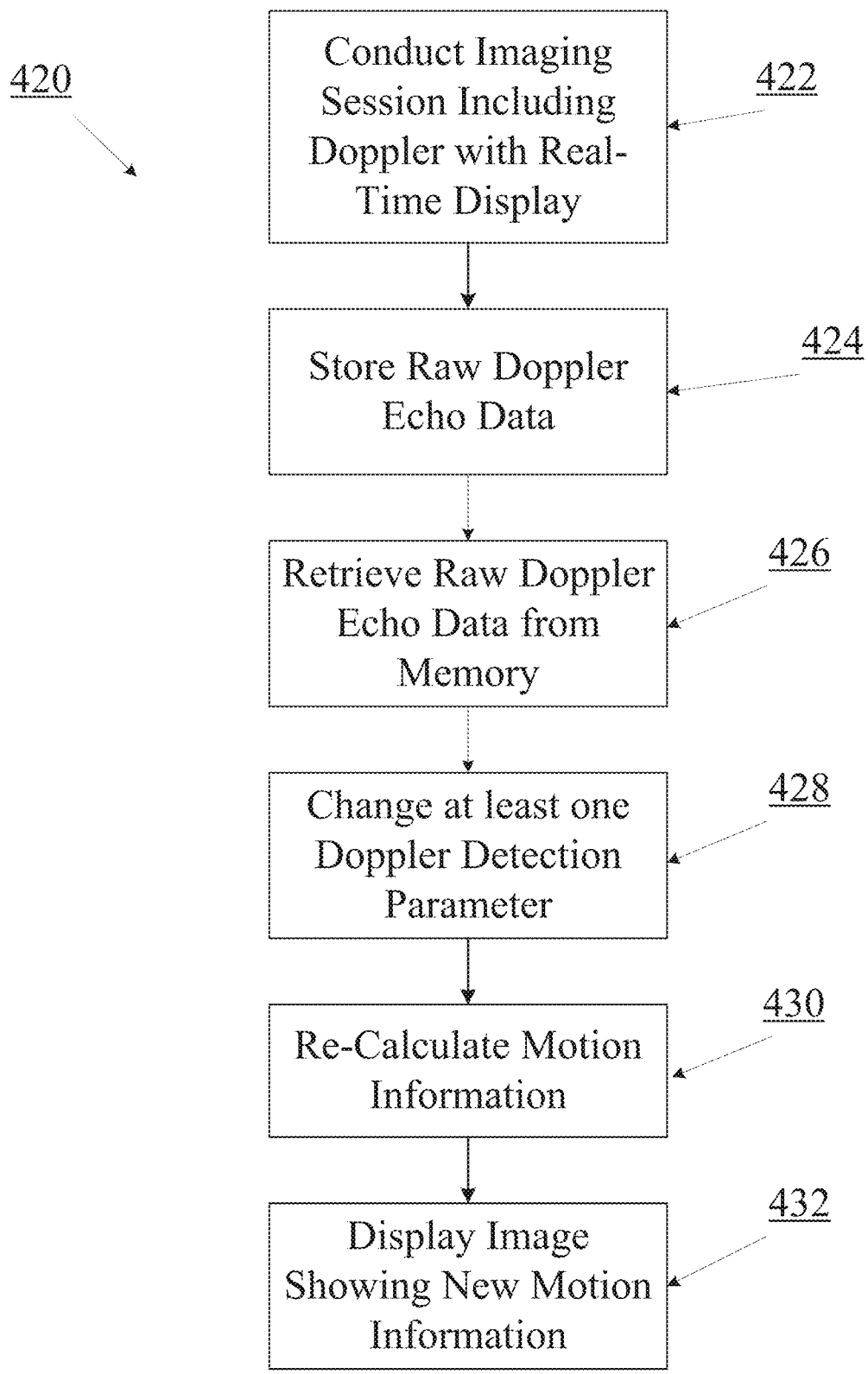
FIG. 21 is a flow chart illustrating an embodiment of a process for re-processing stored Doppler raw echo data.

FIG. 21 illustrates an embodiment of a process 420 for re-processing stored raw Doppler echo data at some time after a live imaging session. During a live imaging session 422 Doppler pings may be transmitted and echoes of such Doppler pings may be received. The raw echo data representing the received echo signals may be stored 424 in a memory device. At some later time, the stored raw Doppler echo data may be retrieved from a memory device 426 and re-processed by changing 428 at least one processing parameter relative to a value used during the live imaging session 422. Motion information may then be re-calculated 430 using the new parameter(s), and a new image derived from the re-calculated motion information may then be displayed 432.

In one example, during a live imaging session, a first image window focused on a particular small-area portion of an insonified region of interest may be selected and displayed while raw echo data may be captured and stored to a memory device. During a session in which the stored echo data is retrieved, a second image window which only partially overlaps the first image window may be defined. In other cases, the second image window may be entirely non-overlapping with the first image window. Similarly, an entirely different color-flow motion axis may be defined in the second image window. As a result, the second image window may be defined to display motion information that was not visible during the live imaging session, either because the selected image window was different or because other assumptions made during a live imaging session may be revised. In some embodiments, echo data from a single imaging session may be beamformed and processed for two or more independent image windows. In such cases, Doppler data may be overlaid in one image window while both image windows are displayed side-by-side. Because both images are generated from the same data set, the moving images of the imaged object will be perfectly synchronized and movement of objects in both (potentially entirely non-overlapping) image windows may be viewed simultaneously to visualize the synchronized action of different regions of the object (e.g., a heart at the same point in the cardiac cycle).

In another example, the definitions of receive "apertures" may be changed when re-processing stored echo data relative to a live imaging session. Because echo data may be stored separately for each receive element, the groupings of transducer elements into receive apertures may be changed at any time. Thus, in some embodiments, if it is determined that a receive aperture assignment used during a live Doppler imaging session was sub-optimal for measuring a particular velocity vector, the receive aperture assignments may be changed, and estimation of velocity vectors using one or more of the methods described above may be repeated in an attempt to improve velocity vector measurements. In some embodiments, a number of receive apertures may be increased or decreased relative to a number of receive apertures used during a live imaging session. In other embodiments, the position of one or more apertures along an array (or multiple arrays) may be changed relative to a position used during a live imaging session.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow. In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

We claim:

1. A method of imaging a moving object with Doppler ultrasound, comprising:
providing a multiple aperture ultrasound probe comprising a first transmit aperture, a first receive aperture, a second receive aperture, and an imaging field that comprises a plurality of pixels, wherein each of the plurality of pixels comprises a first acoustic path to the first receive aperture and a second acoustic path to the second receive aperture;

computing a plurality of adjustment factors for the first acoustic path and the second acoustic path for each of the plurality of pixels;

transmitting a first unfocused spherical ultrasound wavefront pulse from the first transmit aperture towards the moving object;

receiving echoes of the first unfocused spherical ultrasound wavefront pulse at the first receive aperture;

receiving echoes of the first unfocused spherical ultrasound wavefront pulse at the second receive aperture; and computing an object velocity vector at one or more of the plurality of pixels based on the received echoes at the first and second receive apertures and one or more of the plurality of adjustment factors.

2. The method of claim 1, wherein computing the plurality of adjustment factors further comprises:

calculating a first angle between the first transmit aperture and the first acoustic path for each of the plurality of pixels; and calculating a second angle between the first transmit aperture and the second acoustic path for each of the plurality of pixels.

3. The method of claim 1 further comprising: computing a direction of the object velocity vector.

4. The method of claim 1, further comprising computing a magnitude of the object velocity vector.

5. The method of claim 1, wherein a magnitude of the object velocity vector is calculated by taking half the sum of the magnitudes of a first velocity measurement and a second velocity measurement; the first velocity measurement taken along a first acoustic path bisecting an angle between the first receive aperture, one of the plurality of pixels, and the second receive aperture; and the second velocity measurement taken along a second acoustic path from the first transmit aperture to one of the plurality of pixels, to the second receive aperture.

6. The method of claim 1 further comprising: receiving a user input indicating an axis of predominant motion of the moving object.

7. The method of claim 6 further comprising: displaying at least one color to indicate motion along the indicated axis of predominant motion.

8. The method of claim 1 further comprising: automatically analyzing a plurality of measured velocity vectors to identify at least one axis of predominant motion.

9. The method of claim 1, wherein the first unfocused spherical ultrasound wavefront pulse is configured to insonify an entire region of interest.

* * * * *